US010888588B2

(12) United States Patent
Hajjar et al.

(10) Patent No.: US 10,888,588 B2
(45) Date of Patent: Jan. 12, 2021

(54) DIRECTED CARDIOMYOCYTE DIFFERENTIATION AND VENTRICULAR SPECIFICATION OF STEM CELLS

(71) Applicants: ICAHN SCHOOL OF MEDICINE AT MOUNT SINAI, New York, NY (US); THE UNIVERSITY OF HONG KONG, Pokfulam, Hong Kong (CN)

(72) Inventors: Roger Joseph Hajjar, Tenafly, NJ (US); Camie W. Chan, Hong Kong (CN)

(73) Assignees: ICAHN SCHOOL OF MEDICINE AT MOUNT SINAI, New York, NY (US); THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 15/030,325

(22) PCT Filed: Oct. 17, 2014

(86) PCT No.: PCT/US2014/061193
§ 371 (c)(1),
(2) Date: Apr. 18, 2016

(87) PCT Pub. No.: WO2015/058117
PCT Pub. Date: Apr. 23, 2015

(65) Prior Publication Data
US 2016/0271183 A1 Sep. 22, 2016

Related U.S. Application Data

(60) Provisional application No. 61/892,923, filed on Oct. 18, 2013.

(51) Int. Cl.
*A61K 35/34* (2015.01)
*G01N 33/50* (2006.01)
*C12N 5/077* (2010.01)

(52) U.S. Cl.
CPC ............ *A61K 35/34* (2013.01); *C12N 5/0657* (2013.01); *G01N 33/5061* (2013.01); *C12N 2500/02* (2013.01); *C12N 2501/155* (2013.01); *C12N 2501/16* (2013.01); *C12N 2501/415* (2013.01); *C12N 2501/727* (2013.01); *C12N 2501/73* (2013.01); *C12N 2501/999* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| 8,415,155 B2 | 4/2013 | Stankewicz et al. | |
| 2009/0191159 A1* | 7/2009 | Sakurada | C12N 5/0696 424/93.7 |
| 2011/0097799 A1* | 4/2011 | Stankewicz | C12N 5/0657 435/377 |
| 2011/0142935 A1 | 6/2011 | Kamp et al. | |
| 2013/0280809 A1* | 10/2013 | Efe | C12N 5/0602 435/467 |

FOREIGN PATENT DOCUMENTS

| WO | WO 2011159726 A2 * | 12/2011 | ........... C12N 5/0602 |
| WO | 2012/168167 A1 | 12/2012 | |
| WO | 2013/063305 A2 | 5/2013 | |

OTHER PUBLICATIONS

Encyclopedic Reference of Genomics and Proteomics in Molecular Medicine. Normoxia. Springer-Verlag (publisher). First Edition. Copyright 2005-2006.Springer-Verlag. Eds.: Detlev Ganten and Klaus Ruckpaul. Berlin, Heidelberg, Germany. p. 853.*
Mummery, C.L. et al. Jul. 19, 2012. Differentiation of human embryonic stem cells and induced pluripotent stem cells to cardiomyocytes. A methods overview. Circulation Research 111: 344-358. specif. pp. 349, 353.*
Kattman, S.J. et al. 2011. Stage-specific optimization of activin/nodal and BMP signaling promotes cardiac differentiation of mouse and human pluripotent stem cell lines. Cell Stem Cell 8: 228-240. specif. pp. 228, 238.*
Matsa, E. et al. May 26, 2012. In vitro uses of human pluripotent stem cell-derived cardiomyocytes. Journal of Cardiovascular Translational Research 5: 581-592. specif. pp. 581, 583, 584.*
Braam, S.R. et al. 2010. Inhibition of ROCK improves survival of human embryonic stem cell-derived cardiomyocytes after dissociation. Annals of the New York Academy of Sciences 1188: 52-57. specif. p. 52.*
Willems, E. et al. 2011. Small-molecule inhibitors of the Wnt pathway potently promote cardiomyocytes from human embryonic stem cell-derived mesoderm. Circulation Research 109: 360-364. specif. pp. 360, 362, 363.*
Serrao et al., "Myocyte-Depleted Engineered Cardiac Tissues Support Therapeutic Potential of Mesenchymal Stem Cells," Tissue Eng Part A 18(13-14):1322-33 (2012).
International Search Report for corresponding International Application No. PCT/US2014/061193 (dated Feb. 5, 2015).
Written Opinion for corresponding International Application No. PCT/US2014/061193 (dated Feb. 5, 2015).
PCT/US2014/061193, International Preliminary Report on Patentability (dated Apr. 19, 2016).

* cited by examiner

*Primary Examiner* — Renee Claytor
*Assistant Examiner* — Sharon M. Papciak
(74) *Attorney, Agent, or Firm* — Leason Ellis LLP

(57) ABSTRACT

Disclosed is a fully chemically defined, small molecule-mediated, directed differentiation system that promotes differentiation of stem cells, including embryonic stem cells, induced pluripotent stem cells, and adult stem cells, such as human forms of these stem cell types, to ventricular cardiomyocytes in a highly efficient, reproducible and scalable fashion. Also disclosed is a cost-effective and efficient protocol, or method, for generating cardiomyocytes and a cost-effective and efficient method of maturing cardiomyocytes. The disclosed differentiation system provides a platform to perform large-scale pharmacological screenings and to provide a valuable source of each of cardiac progenitor cells and cardiomyocytes for cell replacement therapies in cardiac repair.

13 Claims, 10 Drawing Sheets

Specification includes a Sequence Listing.

A

B

C

D

E

A

B

Control　　　　　　　　　H$_2$O$_2$ 100µM

SEQUENCE LISTING

```
<160> NUMBER OF SEQ ID NOS: 46

<210> SEQ ID NO 1
<211> LENGTH: 23
<212> TYPE: DNA
<213> ORGANISM: Artificial Sequence
<220> FEATURE:
<223> OTHER INFORMATION: Synthetic Primer

<400> SEQUENCE: 1
gcagagtgac atagatcagc ctg                                             23

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer
```

```
<400> SEQUENCE: 2
gcctcaatag gactggctac ca                                              22

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
gctgtgacag gtacccaacc                                                 20

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
catgcaggtg agttgtcaga a                                               21

<210> SEQ ID NO 5
<211> LENGTH: 22
<212> TYPE: DNA
<213> ORGANISM: Artificial Sequence
<220> FEATURE:
<223> OTHER INFORMATION: Synthetic Primer

<400> SEQUENCE: 5
caaggatgca cagtctggcg at                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
gcaggaggaa aaccttcgtg ct                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
aagaggcaga ctgagcggga aa                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
agatgctctg ccacagctcc tt                                              22
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
cacctcaaca gctccctgac                                                     20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
aatgcaaaat ccagggact                                                      20

<210> SEQ ID NO 11
<211> LENGTH: 19
<212> TYPE: DNA
<213> ORGANISM: Artificial Sequence
<220> FEATURE:
<223> OTHER INFORMATION: Synthetic Primer

<400> SEQUENCE: 11
ctgttggaga cctggatgc                                                      19

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
cgtcagttgt cccttgtcac                                                     20

<210> SEQ ID NO 13
<211> LENGTH: 18
<212> TYPE: DNA
<213> ORGANISM: Artificial Sequence
<220> FEATURE:
<223> OTHER INFORMATION: Synthetic Primer

<400> SEQUENCE: 13
gcagccagag tccctcag                                                       18

<210> SEQ ID NO 14
<211> LENGTH: 18
<212> TYPE: DNA
<213> ORGANISM: Artificial Sequence
<220> FEATURE:
<223> OTHER INFORMATION: Synthetic Primer

<400> SEQUENCE: 14
ctggcttttt gcctcctg                                                       18

<210> SEQ ID NO 15
<211> LENGTH: 18
<212> TYPE: DNA
<213> ORGANISM: Artificial Sequence
<220> FEATURE:
<223> OTHER INFORMATION: Synthetic Primer
```

<400> SEQUENCE: 15
cgattcgaaa cccgagag                                                    18

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16
gaaacacttt gattccctcc a                                                21

<210> SEQ ID NO 17
<211> LENGTH: 18
<212> TYPE: DNA
<213> ORGANISM: Artificial Sequence
<220> FEATURE:
<223> OTHER INFORMATION: Synthetic Primer

<400> SEQUENCE: 17
gcaggcggag aggttttc                                                    18

<210> SEQ ID NO 18
<211> LENGTH: 19
<212> TYPE: DNA
<213> ORGANISM: Artificial Sequence
<220> FEATURE:
<223> OTHER INFORMATION: Synthetic Primer

<400> SEQUENCE: 18
agttgccagt cacgtcagg                                                   19

<210> SEQ ID NO 19
<211> LENGTH: 22
<212> TYPE: DNA
<213> ORGANISM: Artificial Sequence
<220> FEATURE:
<223> OTHER INFORMATION: Synthetic Primer

<400> SEQUENCE: 19
ggaacctcac tatccgcaga gt                                               22

<210> SEQ ID NO 20
<211> LENGTH: 22
<212> TYPE: DNA
<213> ORGANISM: Artificial Sequence
<220> FEATURE:
<223> OTHER INFORMATION: Synthetic Primer

<400> SEQUENCE: 20
ccaagttcgt cttttcctgg gc                                               22

<210> SEQ ID NO 21
<211> LENGTH: 22
<212> TYPE: DNA
<213> ORGANISM: Artificial Sequence
<220> FEATURE:
<223> OTHER INFORMATION: Synthetic Primer

<400> SEQUENCE: 21
gtccaggaga tgaggcagaa ac                                               22

```
<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
gtctgcgttc tctttctcca gc                                          22

<210> SEQ ID NO 23
<211> LENGTH: 21
<212> TYPE: DNA
<213> ORGANISM: Artificial Sequence
<220> FEATURE:
<223> OTHER INFORMATION: Synthetic Primer

<400> SEQUENCE: 23
cccgacatcc acttgcgcga g                                           21

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer

<400> SEQUENCE: 24
ggaaggattt cccactctga cg                                          22

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer

<400> SEQUENCE: 25
gggatcgaga catgtaagca g                                           21

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
caagcaagca gaatttggaa                                             20

<210> SEQ ID NO 27
<211> LENGTH: 20
<212> TYPE: DNA
<213> ORGANISM: Artificial Sequence
<220> FEATURE:
<223> OTHER INFORMATION: Synthetic Primer

<400> SEQUENCE: 27
cctcacttca ctgcactgta                                             20

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 28
caggttttgt ttccctagct                                              20

<210> SEQ ID NO 29
<211> LENGTH: 22
<212> TYPE: DNA
<213> ORGANISM: Artificial Sequence
<220> FEATURE:
<223> OTHER INFORMATION: Synthetic Primer

<400> SEQUENCE: 29
ctccaacatc ctgaacctca gc                                           22

<210> SEQ ID NO 30
<211> LENGTH: 23
<212> TYPE: DNA
<213> ORGANISM: Artificial Sequence
<220> FEATURE:
<223> OTHER INFORMATION: Synthetic Primer

<400> SEQUENCE: 30
cgtcacacca ttgctattct tcg                                          23

<210> SEQ ID NO 31
<211> LENGTH: 22
<212> TYPE: DNA
<213> ORGANISM: Artificial Sequence
<220> FEATURE:
<223> OTHER INFORMATION: Synthetic Primer

<400> SEQUENCE: 31
tgagcctcga atccacatag tg                                           22

<210> SEQ ID NO 32
<211> LENGTH: 20
<212> TYPE: DNA
<213> ORGANISM: Artificial Sequence
<220> FEATURE:
<223> OTHER INFORMATION: Synthetic Primer

<400> SEQUENCE: 32
aagcagtcac cgctatgaac                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33 ccacccttt ggagcgaatt                                               20

<210> SEQ ID NO 34
<211> LENGTH: 21
<212> TYPE: DNA
<213> ORGANISM: Artificial Sequence
<220> FEATURE:
<223> OTHER INFORMATION: Synthetic Primer

<400> SEQUENCE: 34
aattagagaa gacggcgtcg g                                            21
```

```
<210> SEQ ID NO 35
<211> LENGTH: 19
<212> TYPE: DNA
<213> ORGANISM: Artificial Sequence
<220> FEATURE:
<223> OTHER INFORMATION: Synthetic Primer

<400> SEQUENCE: 35
caggcccaac gtggttctt                                                19

<210> SEQ ID NO 36
<211> LENGTH: 22
<212> TYPE: DNA
<213> ORGANISM: Artificial Sequence
<220> FEATURE:
<223> OTHER INFORMATION: Synthetic Primer

<400> SEQUENCE: 36
ccatcacgat tctggtcgat ac                                            22

<210> SEQ ID NO 37
<211> LENGTH: 18
<212> TYPE: DNA
<213> ORGANISM: Artificial Sequence
<220> FEATURE:
<223> OTHER INFORMATION: Synthetic Primer

<400> SEQUENCE: 37
ccttgggcga gtgaacgt                                                 18

<210> SEQ ID NO 38
<211> LENGTH: 20
<212> TYPE: DNA
<213> ORGANISM: Artificial Sequence
<220> FEATURE:
<223> OTHER INFORMATION: Synthetic Primer

<400> SEQUENCE: 38
gggtccgctc ccttaagttt                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Primer

<400> SEQUENCE: 39
cagcacagag ctcttcaagc                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic Primer

<400> SEQUENCE: 40
gtccgagatt tcctcctgaa                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 41
gagactgtcg tgggcttgta                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic Primer

<400> SEQUENCE: 42
cttctcaata ggcgcatcag                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic Primer

<400> SEQUENCE: 43
atgagctcct tctccaccac                                               20

<210> SEQ ID NO 44
<211> LENGTH: 21
<212> TYPE: DNA
<213> ORGANISM: Artificial Sequence
<220> FEATURE:
<223> OTHER INFORMATION: Synthetic Primer

<400> SEQUENCE: 44
tccagcaaat tcttgaaatc c                                             21

<210> SEQ ID NO 45
<211> LENGTH: 24
<212> TYPE: DNA
<213> ORGANISM: Artificial Sequence
<220> FEATURE:
<223> OTHER INFORMATION: Synthetic Primer

<400> SEQUENCE: 45
gaaatcccat caccatcttc cagg                                          24

<210> SEQ ID NO 46
<211> LENGTH: 20
<212> TYPE: DNA
<213> ORGANISM: Artificial Sequence
<220> FEATURE:
<223> OTHER INFORMATION: Synthetic Primer

<400> SEQUENCE: 46 gagcccagc cttctccagt                                                20
```

DIRECTED CARDIOMYOCYTE DIFFERENTIATION AND VENTRICULAR SPECIFICATION OF STEM CELLS

This application is a national stage application under 35 U.S.C. § 371 of PCT Application No. PCT/US2014/061193, filed Oct. 17, 2014, which claims the priority benefit of U.S. Provisional Patent Application No. 61/892,923, filed Oct. 18, 2013.

FIELD OF THE INVENTION

The disclosure relates to the field of controlled or directed differentiation of eukaryotic stem cells, such as human stem cells.

BACKGROUND

The adult heart has a limited intrinsic capacity to regenerate lost or damaged myocardium, with ventricular cardiac myocyte deficiency underlying most causes of heart failure. Cardiomyocytes derived from human embryonic stem cells (hESCs) are a potential source for cell replacement therapy, as well as an invaluable tool in the investigation of cardiac development, function, disease modeling and drug testing. Despite considerable progress, however, increasing the efficiency of hESCs to become ventricular cardiomyocytes has been challenging.

The myocardium, i.e., the striated muscle of the heart, is composed of multiple highly specialized myocardial lineages including those of the ventricular and atrial myocardium and the specialized conduction system.[1] An evolutionarily conserved gene regulatory network of transcription factors orchestrates the specification and maturation of each of these lineages during heart development, which is mediated by a plethora of extracellular instructive, spatiotemporally regulated, signaling molecules.[2] Among these molecules are fibroblast growth factors (FGFs), Wnt proteins and members of the transforming growth factor-β (TGF-β) superfamily, including bone morphogenic proteins (BMPs), Activin and Nodal.[3] Similarly, exposing hESCs to a combination of signaling molecules that mimic developmental cues can induce cardiogenesis in vitro.

Current cardiomyocyte differentiation methods generate a low yield and/or a heterogeneous cell population consisting of atrial, pacemaker and ventricular cardiomyocytes.[4-9] The generation of pure populations requires genetic manipulation with viral vectors that enable either drug selection or sorting[10-12], which do not satisfy the criteria for therapeutic applications. In other methods, the stem cells are exposed to a variety of growth factors, and either a P38 inhibitor (see U.S. Pat. Pub. No. 20080187494) or both blebbistatin and Rho-associated kinase (ROCK) (see U.S. Pat. Pub. No. 20110097799). Still other methods are cumbersome and relatively inefficient, such as the four-step method disclosed in U.S. Pat. No. 7,955,849. The existing methods produce insufficient yields, thus precluding their use in therapeutic applications. Additionally, batch-to-batch inconsistency of serum and other animal-based products as well as the high cost of multiple growth factors used in differentiation protocols are prohibitive to large-scale production.

More particularly, Burridge et al. optimized about 45 experimental variables to develop a protocol with optimized concentrations of BMP4 and FGF2, polyvinyl alcohol, serum and insulin for cardiac differentiation of hESCs (H1, H9) and hiPSC lines derived from neonatal CD34$^+$ CB (CBiPSC6.2 and CBiPSC6.11) and adult fibroblasts (iPS-IMR90-1) using non-integrated episomal plasmids to generate 64-89% cTnT$^+$ cells by day 9.[4] The derived CMs are functionally responsive to cardioactive drugs when optically mapped as multi-cellular clusters, but the efficiency and action potential (AP) profiles and distribution of the differentiated CMs were not disclosed and are not expected to approach the levels obtained with the protocols disclosed herein.

In a study by Lian et al., the investigators employed glycogen synthase kinase 3 (GSK3) inhibitors combined with the β-catenin shRNA or a chemical Wnt inhibitor to produce 80-98% purity of functional CMs in 14 days from hESCs (H9, H13, H14) and multiple hiPSC lines (6-9-9, 19-9-11, IMR90C4)[57]. Beating clusters were observed between days 8 and 10. About 20% of day-20 CMs are proliferative, as indicated by Ki67 staining or BrdU assay. The number of cells generated by this protocol is 15 CM per hPSC input without any enrichment and/or purification step. The method focuses on early induction of canonical Wnt signaling and suppression of canonical Wnt signaling at later stages of differentiation to enhance the CM yield.

Zhang et al. reported a matrix sandwich method by overlaying monolayer-cultured human PSCs with Matrigel[2]. The matrix sandwich was combined with sequential applications of activin A, BMP4, and bFGF to generate a high purity of up to 98% and a yield of up to 11 CMs per input PSC from multiple PSC lines, including H1, H9 and three iPSC lines derived from foreskin fibroblasts using non-integrating vectors and the lentiviral-generated iPS cell line IMR90 clone 4 (IMR90 C4). Atrial/ventricular distribution was not reported.

Ren et al. reported that early modulation of the BMP4 coupled with late inhibition of Wnt signaling pathways in human iPSCs to generate high efficiency of cardiac differentiation[14]. This method, tested on H7 only, requires a high concentration of serum (20%) but with a relatively low percentage of cTNT-positive cells (about 16%). AP profiles also were not reported. Minami et al. reported the use of a single small molecule KY02111 to promote hPSC differentiation into CM with a yield of up to 98% by inhibiting WNT signaling[58]. EP data show that VCM and pacemaker cells are present and electrophysiologically functional. The method, tested on four hiPSC lines, can be achieved under serum- and xeno-free condition to produce about 4.2×10$^6$ hPSC-CM from about 6×10$^6$ seeded initially per well, or 0.7 hPSC-CM per hPSC. Given that this method requires only a single small molecule to direct CM differentiation, it is the simplest protocol, but the ventricular yield is unknown.

Recent differentiation methods have led to higher CM yields compared to traditional spontaneous differentiation protocols. However, many of these recently developed methods require optimization of multiple growth factors for different hPSC lines, with variabilities often seen with different hiPSC lines. For example, methods have been disclosed that require an optimization between activin A and BMP4, or that require concentrations of activin A and BMP4 individually optimized for each of various different hESC and hiPSC lines, accompanied by a failure to observe consistently high efficiency and yield of ventricular cardiomyocytes.

For all of the foregoing reasons, needs continue to exist in the art for methods of generating differentiated cells, such as cardiomyocytes, from embryonic stem cells in quantities and at purity levels compatible with safe and cost-effective diagnostic and clinical use. Needs also exist to increase the efficiency of generating cardiomyocytes, such as ventricular cardiomyocytes, from embryonic stem cells and to simplify and/or lower the cost of methods of achieving these benefits.

SUMMARY

The disclosure satisfies at least one of the aforementioned needs in the art by providing a fully chemically defined, two-step differentiation protocol using a combination of recombinant growth factors and small molecules that efficiently promotes the differentiation of embryonic stem cells, including human embryonic stem cells (hESCs), induced pluripotent stem cells (iPS) and adult stem cells, toward ventricular-like cardiomyocytes at the expense of other mesoderm-derived lineages, such as endothelial and smooth muscle. The successful incorporation of small molecules into the protocol provides a reproducible, cost-effective and scalable assay, generating a homogeneous population of ventricular-like cardiomyocytes.

The uses and methods according to the disclosure generate ample quantities of highly purified autologous, or heterologous, cardiomyocytes from stem cells, such as embryonic stem cells, iPS, and adult stem cells. The generation methods only involve two stages and can produce up to and exceeding 90% cardiomyocytes in culture without requiring genetic manipulation or cell sorting. These clinical-grade cardiomyocytes are useful in cell-replacement therapies or transplantations, and are thus useful in treating a variety of cardiovascular conditions, disorders and diseases. The cardiomyocytes generated according to the disclosure are also useful in screening compounds for toxicity, as any compound inhibiting differentiation of stem cells, e.g., embryonic stem cells, to cardiomyocytes in the methods of the disclosure, or any compound inhibiting viability of such cardiomyocytes, would be identified as a compound exhibiting toxic effects. Further, the disclosure provides methods of screening for cardiovascular therapeutics in that candidates that promote differentiation of stem cells, e.g., embryonic stem cells, to cardiomyocytes, or promote the viability of such cardiomyocytes, would be identified as cardiovascular therapeutics.

One aspect of the disclosure is a method of generating a cardiogenic embryoid body comprising at least one cardiomyocyte comprising incubating a non-terminally differentiated human cell in medium comprising effective amounts of BMP4, Rho kinase inhibitor, activin-A and IWR-1. In some embodiments of the method, the non-terminally differentiated human cell is a human embryonic stem cell, a human adult stem cell, or a human induced pluripotent stem cell. In some embodiments, the cardiomyocytes comprise at least one ventricular cardiomyocyte. In some, and perhaps most, embodiments, at least 93% of the cardiomyocytes are cardiac Troponin T+ (cTNT+). Typical embodiments provide cardiomyocytes that exhibit a detectable chronotropic response to β-adrenergic stimulation. In some embodiments, at least 70 ventricular cardiomyocytes (hPSC-VCM) are obtained from each non-terminally differentiated human cell. An exemplary non-terminally differentiated human cell suitable for use in the method is a human pluripotent stem cell (hPSC).

In several embodiments, the non-terminally differentiated human cell is obtained from a subject in need of progenitor cell therapy. In some embodiments, the non-terminally differentiated human cell is incubated in the medium for at least 8 days. In particular embodiments, the following steps are performed: (a) culturing the non-terminally differentiated human cell in mTeSR™ 1 medium comprising 40 µg/ml Matrigel™, 1 ng/ml BMP-4 and 10 µM Rho kinase inhibitor in 5% $O_2$ for 24 hours; (b) washing the culture; (c) incubating the culture in StemPro34 SFM comprising ascorbic acid, GlutaMAX-1, BMP4, and human recombinant activin-A for 3 days; and (d) growing the culture in StemPro34 SFM comprising ascorbic acid, GlutaMAX-1, BMP4, human recombinant activin-A, and IWR-1 for at least four days to generate a culture of cardiomyocytes. For these embodiments, the method may further comprise maintaining the cardiomyocyte culture in StemPro34 SFM comprising 50 µg/ml ascorbic acid in a normoxic environment.

Related aspects of the disclosure provide a method of transplanting autologous cardiomyocytes comprising administering to a subject a therapeutically effective amount of the cardiomyocytes generated according to any of the methods disclosed herein to a subject in need of progenitor cell therapy. Another related aspect provides a method of screening for compound toxicity comprising: (a) incubating cardiomyocytes generated according to any of the methods described herein in the presence or absence of the compound; and (b) determining the toxicity of the compound by measuring the viability of the cardiomyocytes exposed to the compound compared to cardiomyocytes not exposed to the compound. Reduced viability in the presence of the compound is indicative of a toxic compound.

Yet another related aspect of the disclosure is drawn to a method of identifying a cardiovascular therapeutic comprising: (a) incubating a cardiomyocyte generated according to any of the methods disclosed herein in the presence or absence of a compound in medium comprising effective amounts of BMP4, Rho kinase inhibitor, activin-A and IWR-1; and (b) identifying a compound as a cardiovascular therapeutic if the yield of functional cardiomyocytes is greater in the presence compared to the absence of the compound.

Another aspect of the disclosure is a method of maturing a ventricular cardiomyocyte comprising: (a) incubating a cardiomyocyte generated according to any of the methods disclosed herein in media comprising a neurohumoral agent and a histone deacetylase inhibitor; (b) exposing the cardiomyocyte to at least one stressor, such as an electrophysiological stimulus of 1-10 Hz, 1-10 V/cm, 2-10 msec pulses over a stimulation period of 1-28 days, a magnetic bead-based or mechanical stretching by 5-40% elongation, a change of metabolic conditions in the form of a change in the level of at least one metabolite (e.g., addition of oxygen (1-20%), glucose, galactose, or a fatty acid), a change in the level or activity of a compound affecting oxidative stress, a change in the level or activity of a compound inducing a mitochondrial volume increase of at least 20%, a change in the level or activity of a compound inducing a mitochondrial membrane potential hyperpolarization of at least three-fold, a change in the level or activity of a compound inducing an increase in mitochondrial citrate synthase activity of at least 60%, a change in the level or activity of a compound inducing a change in a cell shape factor of at least 30%, a decrease in cell death rate of at least 30% resulting from a cellular insult, a detectable change in electrophysiological and/or mechanobiological profiles indicative of developmental maturation, a change in the level or activity of a compound that induces expression of peroxisome-proliferator-activated receptor alpha (PPAR-alpha), or any combination of the above changes in metabolic conditions; and (c) contacting the cardiomyocyte with an adrenergic/cholinergic agonist (e.g., 10-500 nM isoproterenol), thereby generating a mature cardiomyocyte. In some embodiments, the incubating step is performed under hypoxic or hyperoxic conditions. The incubating step may also be performed under normoxic conditions.

In some embodiments, the neurohumoral agent is selected from the group consisting of thyroid hormone T3 and an adrenergic agonist. An exemplary histone deacetylase inhibitor useful in the methods is valproic acid. Suitable hypoxic conditions for use in the method include, but are not limited to, 5% $O_2$. In some embodiments, the stressor comprises a change of metabolic conditions such as the added exposure to oxygen (1-20%), the addition of glucose (e.g., 1-50 mM) and/or galactose (e.g., 1-50 mM), the addition of at least one fatty acid (e.g., 0.1-1 mM fatty acid such as oleic acid or oleate), an oxidative stress condition (e.g., addition of 10-300 μM $H_2O_2$) as well as a change in a physiological or pathophysiological metabolic condition known in the art to be associated with a stressor (e.g., normal individuals and arrhythmogenic right ventricular dysplasia (ARVD) patients are known to activate PPAR-alpha-dependent metabolism differently[80]) for mimicking in vivo conditions. In some embodiments, the change of metabolic conditions comprises a change in the concentration or activity of at least one of glucose, a fatty acid, oxidation stress, a metabolite, or a modulator of a metabolic protein, such as an ATP-sensitive potassium (KATP) channel (including both mitochondrial and sarcolemmal channels), Permeability Transition Pore (PTP), as well as other key metabolic and related pathways proteins such as Peroxisome proliferator-activated receptor gamma coactivator 1-alpha and -beta (PGC1α and β), poly(ADP-ribose)polymerase (PARP), AMP-activated protein kinase (AMPK), and the like, and their modulators (e.g., reactive oxygen species, the PARP inhibitor L-2286). Modulators of KATP include higher glucose and increased levels of ATP, which induce KATP channels to close. Modulators in the form of inhibitors of PTP include the immune suppressant cyclosporine A (CsA); N-methyl-Val-4-cyclosporin A (MeValCsA), a non-immunosuppressant derivative of CsA; another non-immunosuppressive agent, NIM811 (N-methyl-4-isoleucine cyclosporin); 2-aminoethoxydiphenyl borate (2-APB); [19] bongkrekic acid and alisporivir (also known as Debio-025). Other factors that increase the likelihood that the PTP will be induced include acidic conditions, high concentrations of ADP, high concentrations of ATP, and high concentrations of NADH (Nicotinamide Adenine Dinucleotide Hydrate). Other metabolic proteins and compounds include pyruvate, acetyl coenzymeA (acetyl coA), glucose, lactose, fructose and glucosamine. Electrophysiological, and contractile maturation, as well as mitochondrial polarization, stability, and structure (mitochondrial morphometry analysis, including form factor, circularity, and area) are considered to be maturation signs.

In some embodiments of the method of maturing a ventricular cardiomyocyte, the adrenergic agonist is selected from the group consisting of epinephrine, nor-epinephrine, adrenaline, an alpha-1A adrenergic agonist, an alpha-1B adrenergic agonist, an alpha-1D adrenergic agonist, an alpha-2A adrenergic agonist, an alpha-2B adrenergic agonist, an alpha-2C adrenergic agonist, a beta-1 adrenergic agonist, a beta-2 adrenergic agonist, a beta-3 adrenergic agonist and any other adrenergic agonist known in the art, including the following adrenergic agonists, which are not readily classifiable in the above system. Methoxamine, methylnorepinephrine, midodrine, oxymetazoline, metaraminol, phenylephrine, clonidine, guanfacine, guanabenz, guanoxabenz, guanethidine, xylazine, tizanidine, methyldopa, fadolmidine, dexmedetomidine, amidephrine, amitraz, anisodamine, apraclonidine, brimonidine, cirazoline, detomidine, dexmedetomidine, epinephrine, ergotamine, etilefrine, indanidine, lofexidine, medetomidine, mephentermine, metaraminol, methoxamine, mivazerol, naphazoline, norepinephrine, norfenefrine, octopamine, oxymetazoline, phenylpropanolamine, rilmenidine, romifidine, synephrine, talipexole, dobutamine, β1 isoproterenol, β2 isoproterenol, xamoterol, epinephrine, salbutamol (albuterol), levosalbutamol (levalbuterol), fenoterol, formoterol, metaproterenol, salmeterol, terbutaline, clenbuterol, isoetarine, pirbuterol, procaterol, ritodrine, arbutamine, befunolol, bromoacetylalprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol and zinterol.

An exemplary adrenergic agonist suitable for use in the method of maturing a ventricular cardiomyocyte is selected from the group consisting of methoxamine, methylnorepinephrine, midodrine, oxymetazoline, metaraminol, phenylephrine, clonidine, guanfacine, guanabenz, guanoxabenz, guanethidine, xylazine, tizanidine, methyldopa, fadolmidine, dexmedetomidine, amidephrine, amitraz, anisodamine, apraclonidine, brimonidine, cirazoline, detomidine, dexmedetomidine, epinephrine, ergotamine, etilefrine, indanidine, lofexidine, medetomidine, mephentermine, metaraminol, methoxamine, mivazerol, naphazoline, norepinephrine, norfenefrine, octopamine, oxymetazoline, phenylpropanolamine, rilmenidine, romifidine, synephrine, talipexole, dobutamine, β1 isoproterenol, β2 isoproterenol, xamoterol, epinephrine, salbutamol (albuterol), levosalbutamol (levalbuterol), fenoterol, formoterol, metaproterenol, salmeterol, terbutaline, clenbuterol, isoetarine, pirbuterol, procaterol, ritodrine, arbutamine, befunolol, bromoacetylalprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol and zinterol.

In some embodiments of the method of maturing a ventricular cardiomyocyte, a cholinergic agonist is used. An exemplary cholinergic agonist suitable for use in the method of maturing a ventricular cardiomyocyte is selected from the group consisting of acetylcholine, bethanechol, carbachol, methacholine, arecoline, nicotine, muscarine, pilocarpine, donepezil, edrophonium, neostigmine, physostigmine, pyridostigmine, rivastigmine, tacrine, caffeine, huperzine, echothiophate, isoflurophate, cisapride, droperidol, domperidone, metoclopramide, risperidone and paliperidone.

For this aspect, and for all other aspects of this disclosure, fragments, variants and fusions of the medium components are contemplated, on the condition that they provide the activity of BMP4, Rho kinase inhibitor, activin-A and IWR-1, as will be apparent from the context.

Particular aspects and embodiments of the disclosure are described in the following enumerated claims.

1. A method of generating a cardiogenic embryoid body comprising at least one cardiomyocyte comprising incubating a non-terminally differentiated human cell in medium comprising effective amounts of BMP4, Rho kinase inhibitor, activin-A and IWR-1.

2. The method according to claim 1, wherein the non-terminally differentiated human cell is a human embryonic stem cell, a human adult stem cell, or a human induced pluripotent stem cell.

3. The method according to any one of claims 1 and 2, wherein the cardiomyocytes comprise at least one ventricular cardiomyocyte.

4. The method according to any one of claims 1-3, wherein at least 93% of the cardiomyocytes are cardiac Troponin T+ (cTNT+).

5. The method according to any one of claims 1-4, wherein the cardiomyocytes exhibit a detectable chronotropic response to β-adrenergic stimulation.

6. The method according to any of claims 1-5, wherein at least 70 ventricular cardiomyocytes (hPSC-VCM) are obtained from each non-terminally differentiated human cell.

7. The method according to claim 6, wherein the non-terminally differentiated human cell is a human pluripotent stem cell (hPSC).

8. The method according to any one of claims 1-7, wherein the non-terminally differentiated human cell is obtained from a subject in need of progenitor cell therapy.

9. The method according to claims 1, wherein the non-terminally differentiated human cell is incubated in the medium for at least 8 days.

10. The method according to claim 1, comprising the following steps:
   (a) culturing the non-terminally differentiated human cell in mTeSR™ 1 medium comprising 40 µg/ml Matrigel™, 1 ng/ml BMP-4 and 10 µM Rho kinase inhibitor in 5% $O_2$ for 24 hours;
   (b) washing the culture;
   (c) incubating the culture in StemPro34 SFM comprising ascorbic acid, GlutaMAX-1, BMP4, and human recombinant activin-A for 3 days; and
   (d) growing the culture in StemPro34 SFM comprising ascorbic acid, GlutaMAX-1, BMP4, human recombinant activin-A, and IWR-1 for at least four days to generate a culture of cardiomyocytes.

11. The method according to claim 10, further comprising maintaining the cardiomyocyte culture in StemPro34 SFM comprising 50 µg/ml ascorbic acid in a normoxic environment.

12. A method of transplanting autologous cardiomyocytes comprising administering to a subject a therapeutically effective amount of the cardiomyocytes generated according to any one of claim 1-8, to a subject in need of progenitor cell therapy.

13. A method of screening for compound toxicity comprising:
   (a) incubating cardiomyocytes generated according to any one of claims 1-8, in the presence or absence of the compound; and
   (b) determining the toxicity of the compound by measuring the viability of the cardiomyocytes exposed to the compound compared to cardiomyocytes not exposed to the compound.

14. A method of identifying a cardiovascular therapeutic comprising:
   (a) incubating a cardiomyocyte generated according to any one of claims 1-8, in the presence or absence of a compound in medium comprising effective amounts of BMP4, Rho kinase inhibitor, activin-A and IWR-1; and
   (b) identifying a compound as a cardiovascular therapeutic if the yield of functional cardiomyocytes is greater in the presence compared to the absence of the compound.

15. A method of maturing a ventricular cardiomyocyte comprising:
   (a) incubating a cardiomyocyte generated according to any one of claims 1-8, in media comprising a neurohumoral agent and a histone deacetylase inhibitor;
   (b) Exposing the cardiomyocyte to at least one stressor, such as an electrophysiological stimulus of 1-10 Hz, 1-10 V/cm, 2-10 msec pulses over a stimulation period of 1-28 days, a magnetic bead-based or mechanical stretching by 5-40% elongation, a change of metabolic conditions in the form of a change in the level of at least one metabolite (e.g., oxygen (1-20%), glucose, galactose, and/or a fatty acid), a change in the level or activity of a compound affecting oxidative stress, a change in the level or activity of a compound inducing a mitochondrial volume increase of at least 20%, a change in the level or activity of a compound inducing a mitochondrial membrane potential hyperpolarization of at least three-fold, a change in the level or activity of a compound inducing an increase in mitochondrial citrate synthase activity of at least 60%, a change in the level or activity of a compound inducing a change in a cell shape factor of at least 30%, a decrease in cell death rate of at least 30% resulting from a cellular insult, a detectable change in electrophysiological and mechanobiological profiles indicative of developmental maturation, or a change in the level or activity of a compound that induces expression of peroxisome-proliferator-activated receptor alpha (PPAR-alpha), or any combination of the above changes in metabolic conditions; and
   (c) contacting the cardiomyocyte with an adrenergic/cholinergic agonist, thereby generating a mature cardiomyocyte.

16. The method according to claim 15, wherein the incubating step is performed under hypoxic or hyperoxic conditions.

17. The method according to claim 15, wherein the neurohumoral agent is selected from the group consisting of thyroid hormone T3 and an adrenergic agonist.

18. The method according to claim 15, wherein the histone deacetylase inhibitor is valproic acid.

19. The method according to claim 15, wherein the hypoxic conditions comprise 5% $O_2$.

20. The method according to claim 15, wherein the change of metabolic conditions comprises the addition of at least one of 1-50 mM glucose, 1-50 mM galactose, 0.1 mM oleic acid, or 10-300 µM $H_2O_2$.

21. The method according to claim 15, wherein the adrenergic agonist is selected from the group consisting of epinephrine, nor-epinephrine, adrenaline, an alpha-1A adrenergic agonist, an alpha-1B adrenergic agonist, an alpha-1D adrenergic agonist, an alpha-2A adrenergic agonist, an alpha-2B adrenergic agonist, an alpha-2C adrenergic agonist, a beta-1 adrenergic agonist, a beta-2 adrenergic agonist, and a beta-3 adrenergic agonist.

22. The method according to claim 21, wherein the adrenergic agonist is selected from the group consisting of methoxamine, methylnorepinephrine, midodrine, oxymetazoline, metaraminol, phenylephrine, clonidine, guanfacine, guanabenz, guanoxabenz, guanethidine, xylazine, tizanidine, methyldopa, fadolmidine, dexmedetomidine, amidephrine, amitraz, anisodamine, apraclonidine, brimonidine, cirazoline, detomidine, dexmedetomidine, epinephrine, ergotamine, etilefrine, indanidine, lofexidine, medetomidine, mephentermine, metaraminol, methoxamine, mivazerol, naphazoline, norepinephrine, norfenefrine, octopamine, oxymetazoline, phenylpropanolamine, rilmenidine, romifidine, synephrine, talipexole, dobutamine, β1 isoproterenol, β2 isoproterenol, xamoterol, epinephrine, salbutamol (albuterol), levosalbutamol (levalbuterol), fenoterol, formoterol, metaproterenol, salmeterol, terbutaline, clenbuterol, isoetarine, pirbuterol, procaterol, ritodrine, arbutamine, befunolol, bromoacetylalprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol and zinterol.

23. The method according to claim 15, wherein the cholinergic agonist is selected from the group consisting of acetylcholine, bethanechol, carbachol, methacholine, arecoline, nicotine, muscarine, pilocarpine, donepezil, edrophonium, neostigmine, physostigmine, pyridostigmine, rivastigmine, tacrine, caffeine, huperzine, echothiophate, isoflurophate, cisapride, droperidol, domperidone, metoclopramide, risperidone and paliperidone.

Other features and advantages of the disclosure will be better understood by reference to the following detailed description, including the drawing and the examples.

DETAILED DESCRIPTION

Figure 1:
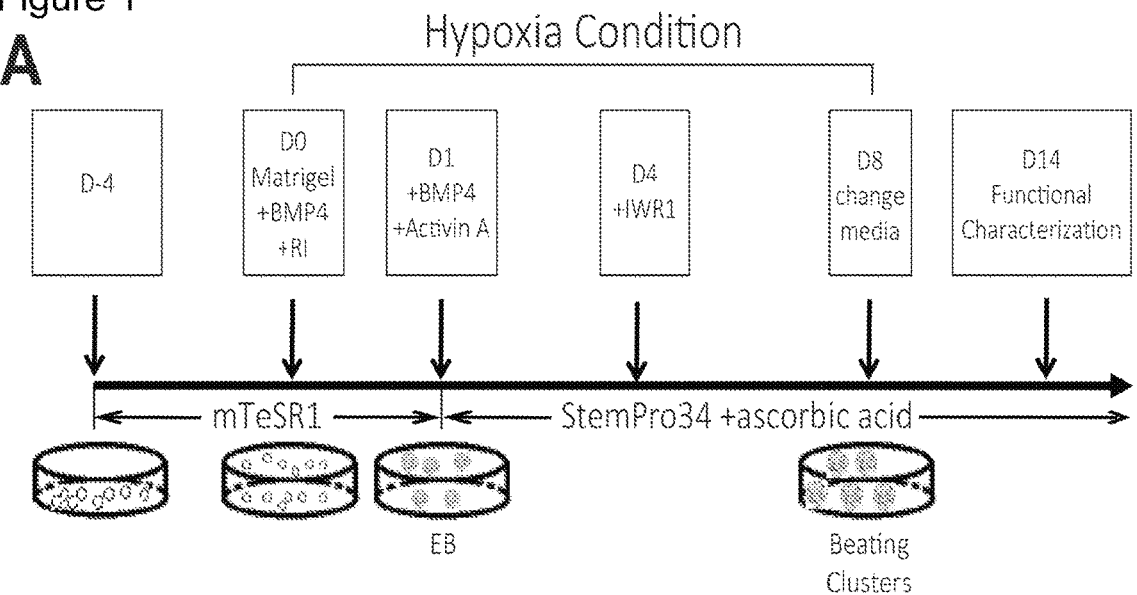
FIG. 1. A highly efficient VCM differentiation system of hPSCs. (A) Schematic of a direct differentiation protocol used for the differentiation of hPSCs to VCMs under non-feeder and non-xenogeneic conditions. Spontaneously contracting clusters were detected as early as day 8. (B) Images demonstrate typical culture morphology at different time points of differentiation. Scale bar=200 μm.
Figure 1:
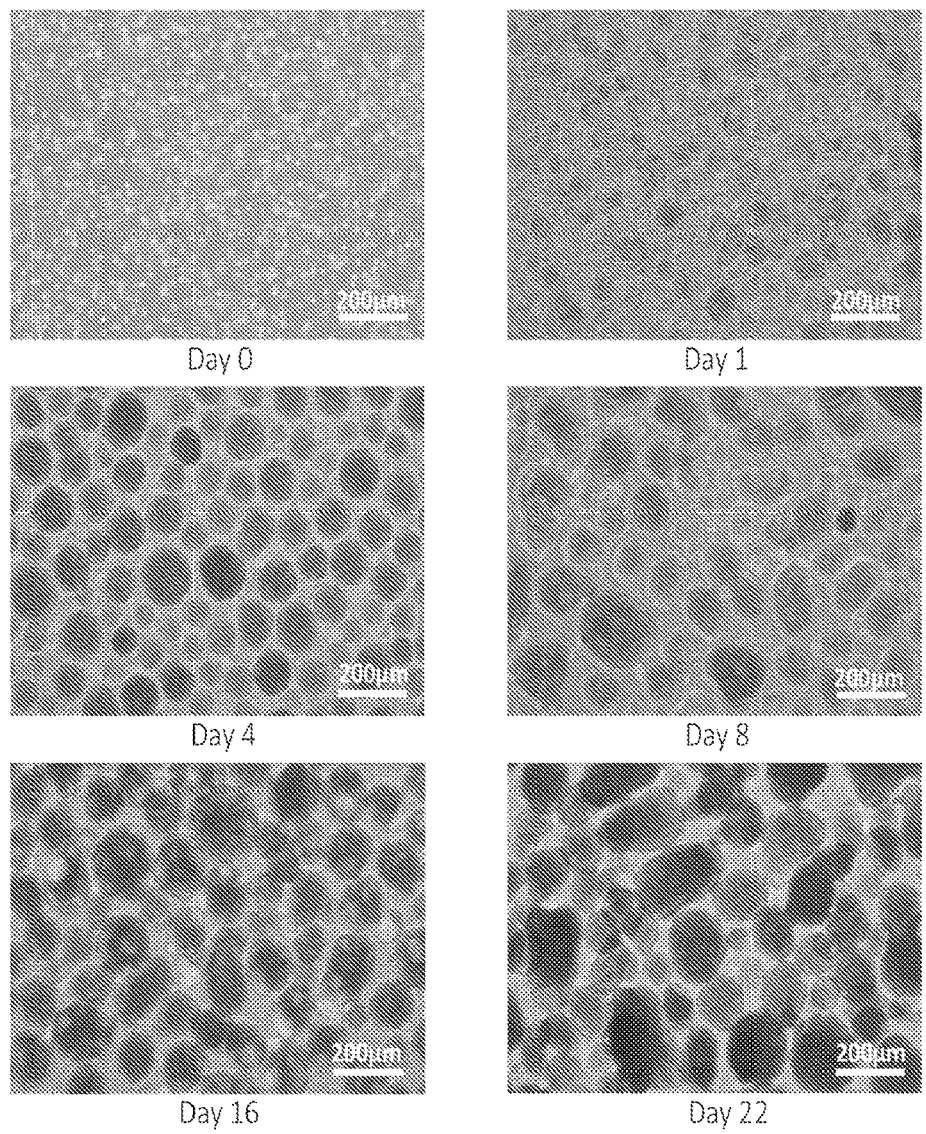

The generation of human ventricular cardiomyocytes from stem cells, such as embryonic stem cells (e.g., human embryonic stem cells or hESCs), induced pluripotent stem cells or adult stem cells, in particular human forms of one of these stem cell types, will fulfill a long-standing demand for such cells in therapeutic applications. The inability to produce large, pure populations with existing protocols remains a major limitation, however. The disclosure provides combinations of small molecules and growth factors in a chemically defined, direct differentiation protocol that differentiates stem cells such as embryonic stem cells (e.g., hESCs), induced pluripotent stem cells and adult stem cells toward ventricular cardiomyocytes in an efficient, reproducible and scalable fashion. Phenotypic and molecular analyses demonstrated the generation of a nearly pure population of ventricular cardiomyocytes (>90%). The chemically induced ventricular cardiomyocytes (termed ciVCMs) exhibited the appropriate phenotypic, electrophysiological, and calcium handling characteristics; the ciVCMs also responded appropriately to chronotropic compounds. Collectively, the data indicate that the disclosed methods recapitulate the human cardiac developmental program and generate a high yield of functional ventricular cardiomyocytes. These methods also provide an efficient experimental platform that is expected to facilitate large-scale pharmacological screening and provide a source of ventricular cardiomyocytes for cell replacement therapies.

One aspect of the disclosure provides a method, or protocol, for directed differentiation that efficiently yields significant quantities of ventricular cardiomyocytes. The protocol provides the benefit of producing a final output of about 35-70 hPSC-VCMs per hPSC (compared to 1-20 hPSC-CMs per hPSC, of which a fraction was VCMs). Additionally, the protocol provides a relatively simple and cost-effective method for reproducibly generating cardiac cells within a short time while requiring lower quantities of, and/or fewer, reagents (e.g., bFGF and VEGF were not needed for expansion). Further this protocol is effective for multiple hESC and hiPSC lines without the need of line-dependent optimization. Moreover, the ventricular specification of hESC/iPSC has been confirmed electrophysiologically by ventricular AP and ionic currents.

In the protocol according to this aspect of the disclosure, undifferentiated hPSCs are digested into clusters and seeded onto Matrigel™-coated plates at $1\text{-}10 \times 10^4$ cells/ml until they reach about 80-95% confluence on day 0 (D0). Cells can be cultured in medium other than Matrigel-coated plates and mTeSR with Matrigel, such as E8 with vitronectin or Geltrex, or other media known in the art as suitable for culturing cells that have not yet terminally differentiated. Seeding concentrations are not crucial as long as the target confluency is reached.

In general terms, under the protocol cardiac differentiation is initiated by digesting hPSCs into single-cell suspensions (e.g., by accutase (Invitrogen), dispase, trypsin and/or other means known in the art) and cultured (e.g., mTeSR™ 1 medium with Matrigel™, or a comparable medium) with BMP-4 (0.5-20 ng/ml, Invitrogen) and Rho kinase inhibitor (ROCK) Inhibitor (5-50 µM; R&D). Twenty-four to seventy-two hours later, the culture is washed and replaced with ascorbic acid (AA, 50 µg/ml; Sigma), 2 mM GlutaMAX-1 (Invitrogen), BMP4 (5-25 ng/ml) and human recombinant activin-A (2-25 ng/ml; Invitrogen) in a suitable culture media (e.g., StemPro34 SFM, Invitrogen) for 3-5 days (ascorbic acid and GlutaxMax on Day 2 are recommended, but may not be absolutely needed). On the following day, a Wnt inhibitor, (e.g., IWR-1, 4-7 µM; Enzo Life Sciences) is added. With this method, cardiac mesodermal cells developed into functional contracting clusters can be detected as early as day 8. In the attached manuscripts, particular combinations tested are given. On day 8 or subsequently, cardiomyocytes, primarily ventricular cardiomyocytes, with a yield of over 90%, are transferred to a normoxic environment and maintained in medium for further characterization or maturation.

It has been observed that Matrigel appears to promote the survival of hESCs. If there is no Matrigel on day 0, cluster formation does not occur for cells from the iPSC, H7 and H9 cell lines on day 1; and for cells from the HES2 line, there may be significantly less cluster formation without Matrigel and therefore lower cardiomyocyte yields. Moreover, others have reported that ROCK inhibitor affects normal heart development in mice. If cell survival is not promoted, cardiomyocyte development may be compromised. If there is too much ROCK inhibitor (10 µM, R&D), clusters may overgrow and thereby negatively affect cardiomyocyte yield (which appears to be cluster size-dependent). Further, precise optimization of Activin A and BMP4 signaling for each of the hESC and iPSC lines may facilitate efficient cardiac differentiation in EB.[46] Therefore, it may be advantageous to titrate these compounds depending on the specific PSC line(s). Another general observation relevant to use of the protocol is that differentiation between Day 0 to 8 can be done in hypoxic or normoxic conditions. However, action potential and other functional, structural profiles of the (ventricular) cardiomyocytes derived may differ slightly depending on whether differentiation occurred under hypoxic or normoxic or even hyperoxic conditions.

Human pluripotent stem cells and cardiomyogenic progenitors represent an unlimited ex vivo source of human CMs. Although early cardiac differentiation events can now be reasonably captured in vitro, most stem cell-derived CMs reported to date have been heterogeneous, with immature cardiac phenotypes. To overcome this major roadblock and develop a physiological adult-like in vitro heart surrogate for improved tissue and disease modeling, cardiotoxicity and drug discovery applications, another aspect of the disclosure provides a method to drive maturation once cardiomyocytes are formed (e.g., using the protocol above to generate such cardiomyocytes). Specifically, a multiplexed temporal variation of developmentally relevant metabolic, neurohumoral and biomimetic cues are needed to trigger molecular and signaling events that more completely recapitulate the micro-environmental niches of the native human myocardium.

To maximize maturation, a 3-stage combinatorial method is applied to the (ventricular) cardiomyocytes obtained according to a protocol disclosed herein, such as the protocol described above. During stage 1, hESC-VCMs are primed for maturation to promote a more effective outcome when Stage 2 signals are given. The objective is to provide the molecular and epigenetic/transcriptomic machinery needed, such that hESC-VCMs will become responsive to Stage 2 signals and be ready to mature. Based on experimental data, priming is accomplished by applying at least one of the following pre-natal biomimetics, namely a) hypoxia (5% $O_2$ upregulates sarcoKATP, HIF1a, and the like), b) developmentally relevant neurohumoral agents (such as thyroid hormone T3 which increases cell volume, adrenergic mediators such as a1AR, PAR and combined a/pARs, using PE, Iso, epinephrine (Epi) or norepinephrine (NE), respectively), c) HDAC inhibitor (e.g., Valproic acid or VPA, to stage the epigenetic landscape and induce hypertrophic growth), or combinations of any one or more of a) to c). Stage 2 is the dynamic loading stage. Once the cells are primed, it is expected that Stage 2 signals will more readily drive maturation. The stage 2 signals, or inputs, can be and are considered to be cellular stressors. These stage 2 stressors are a) electrophysiological (e.g., i) stimulating frequency of 1, 3, 10 Hz, ii) voltage at 1, 2.5, 10 V/cm, iii) pulse duration of 2, 5, 10 msec, and iv) stimulation period for 1, 3, 7 days, 4 weeks), b) mechanical or magnetic bead-based stretching by 5-40% elongation, and c) metabolic loads (by altering the metabolic/energetic demand under normal, various fatty acid/glucose conditions and oxidative stresses are systematically and combinatorially given to primed human cardiomyocytes or their multi-cellular tissue constructs as stressors functioning as stimulating signals that mimic the post-natal changes of fetal heart development.

Specifically, these "pro-maturation" stimuli are given by pacing (electrophysiological stimulation), mechanical or magnetic bead-based stretching, and/or change of metabolic conditions, respectively. Exposing metabolic loads include a change of metabolic conditions in the form of a change in the level of at least one metabolite (e.g., oxygen (1-20%), glucose, galactose, and/or a fatty acid), a change in the level or activity of a compound affecting oxidative stress, a change in the level or activity of a compound inducing a mitochondrial volume increase of at least 20%, a change in the level or activity of a compound inducing a mitochondrial membrane potential hyperpolarization of at least three-fold, a change in the level or activity of a compound inducing an increase in mitochondrial citrate synthase activity of at least 60%, a change in the level or activity of a compound inducing a change in a cell shape factor of at least 30%, a decrease in cell death rate of at least 30% resulting from a cellular insult, a detectable change in electrophysiological and mechanobiological profiles indicative of developmental maturation, or a change in the level or activity of a compound that induces expression of peroxisome-proliferator-activated receptor alpha (PPAR-alpha), or any combination of the above changes in metabolic condition. In some embodiments, the change of metabolic conditions comprises the addition of at least one of 1-50 mM glucose, 1-50 mM galactose, 0.1 mM oleic acid, or 10-300 µM $H_2O_2$. In the Stage 3 wiring phase of the maturation protocol, adrenergic/cholinergic agonists are applied to mimic neuronal effects on maturing hESC-VCMs for promoting their wiring to extracellular and intracellular signaling cascades. In some embodiments, an adrenergic agonist is brought into contact with the cardiomyocyte to be matured; in other embodiments, the cell contacts a cholinergic agonist. As already described, neuronal inputs and release of Epi (i.e., epinephrine) also occur intermittently during pre-, peri- and post-natal development. Therefore, neuro-mimetics will be applied during pre-natal and post-natal (early and late) periods.

The maturation protocol, as generally described above, is performed using conventional cultures or tissues (e.g., microtissues, tissue strips or organoid chamber) to provide a suitable environment or context. The disclosed methods lead to cells or tissue constructs that accurately mimic "human" hearts, thereby providing an invaluable resource for the analysis of gene defects, for toxicology studies, and even for designing future transplantable constructs.

The chemical biology approach used herein takes advantage of readily available and inexpensive synthetic bioactive molecules that regulate stem cell fate. Described herein is the development of a fully chemically defined, small molecule-mediated directed method that drives differentiation of stem cells, such as human embryonic stem cells, toward ventricular cardiomyocytes. This method is reproducible, cost efficient, scalable and generates a large number of nearly pure ventricular cardiomyocytes that reach clinical-grade purity without genetic manipulation or cell sorting. The generation of a renewable source of readily available ventricular cardiomyocytes provides a platform for regenerative cell-based therapies as well as drug discovery and toxicity screening.

Figure 6:
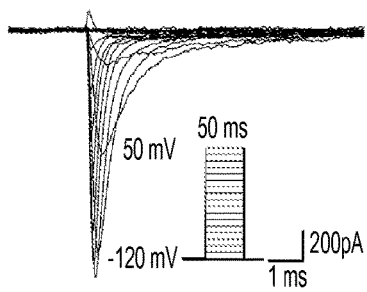
FIG. 6. Ionic currents ($I_{Na}$, $I_{CaL}$, $I_{Kr}$, $I_{KATP}$) in HES2-CMs. Representative (A) $I_{Na}$ and (B) $I_{CaL}$ traces elicited by voltage protocol shown in inset. Middle: Peak I-V plots. Right: Steady-state inactivation and activation relations. (n>7). (C) Representative $I_{Kr}$ traces after the subtraction of E4031-insensitive current elicited by voltage protocol shown in inset. (D) Activation relation of $I_{kr}$ (n=11). (E) Sarcolemmal $I_{KATP}$ channels in HES2-VCMs. Left panel: Representative tracings of sarcolemmal $I_{KATP}$ in HES2-VCMs at 0 mV under control conditions (blue line), with sodium cyanide (CN, 2 mM) alone (black line), or with CN and glibenclamide (GLI, 10 μM; red line). Right panel: Summary of averaged current densities under the same conditions. Cells were stimulated to 0 mV for 1000 ms from a holding potential of −80 mV preceded by a 100-ms prepulse to −10 mV (n=5). **P<0.01 compared to control group; ## P<0.01 compared to CN group.
Figure 6:
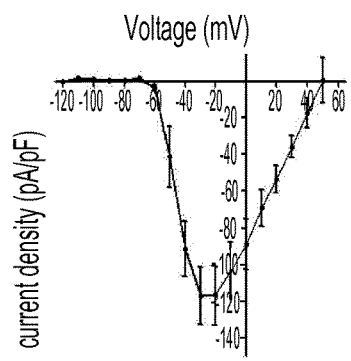
Figure 6:
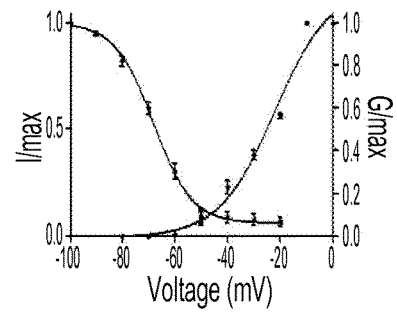
Figure 6:
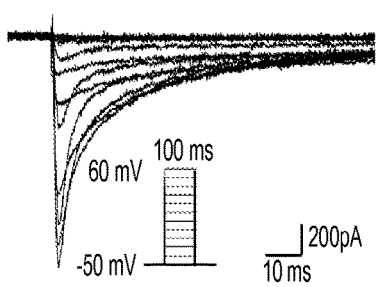
Figure 6:
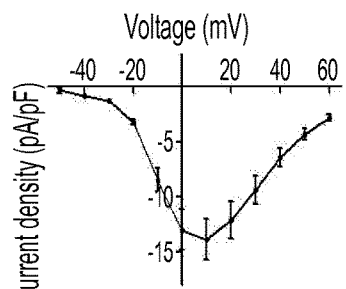
Figure 6:
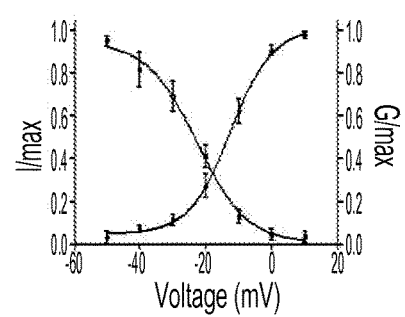
Figure 6:
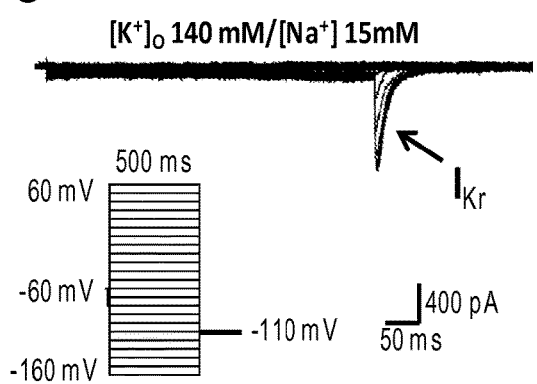
Figure 6:
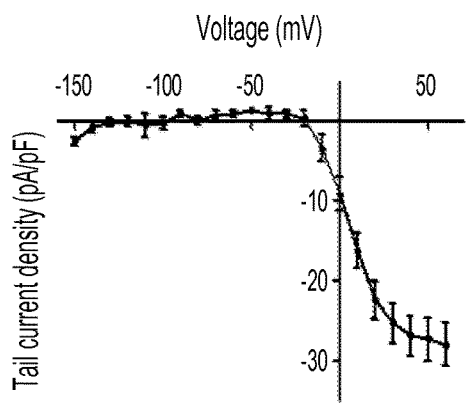
Figure 6:
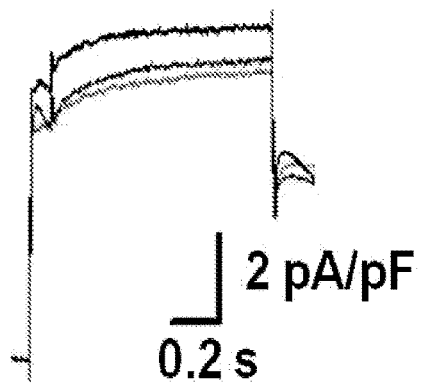
Figure 6:
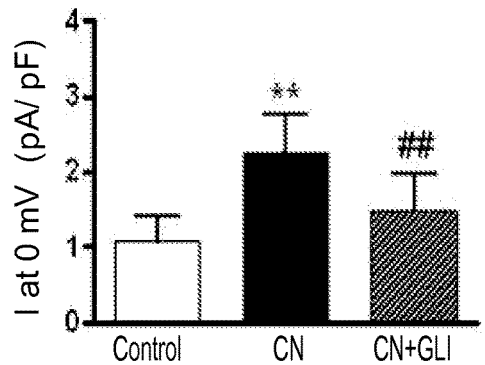

A better understanding of the signaling pathways during development has led to the development of assays to control cardiomyocyte specification in vitro. Current protocols are relatively inefficient with low percentage of a heterogeneous population of cardiomyocytes, however, indicating a need for further refinement. Described herein is a fully chemically defined, two-step differentiation method using a combination of protein growth factors and small molecules that effectively promotes the differentiation of stem cells such as hESCs toward cardiomyocytes at the expense of other mesoderm-derived lineages, including endothelial and smooth muscle cell lineages (FIG. 6). The successful incorporation of well-characterized small molecules into the method provides a reproducible, cost efficient and scalable methodology, which generates a large number of nearly pure ventricular cardiomyocytes.

As detailed in the following examples, cardiac differentiation was initiated by formation of embryoid bodies (EBs) in suspension culture from hESCs as exemplary stem cells, maintained in feeder-free, serum-free culture. The cardiogenic EBs were formed in the presence of the small molecule blebbistatin, a myosin inhibitor known to efficiently suppress the dissociation-induced apoptosis of hESCs.[19, 20] As a result of the blebbistatin treatment, apoptosis was inhibited and EB formation efficiency was significantly increased. In the first phase of the differentiation process (Stage 1; days 2-4.5), the cells were differentiated into primitive streak-mesendoderm and subsequently to cardiac mesoderm by the combinatorial activation of the BMP and Nodal signaling pathways. In the second phase (Stage 2; days 4.5-8) the inhibition of the Wnt/β-catenin pathway by the small molecule IWR-1[29] enhanced the differentiation of the cardiac progenitors to the ventricular cardiomyocyte lineage.

Figure 2:
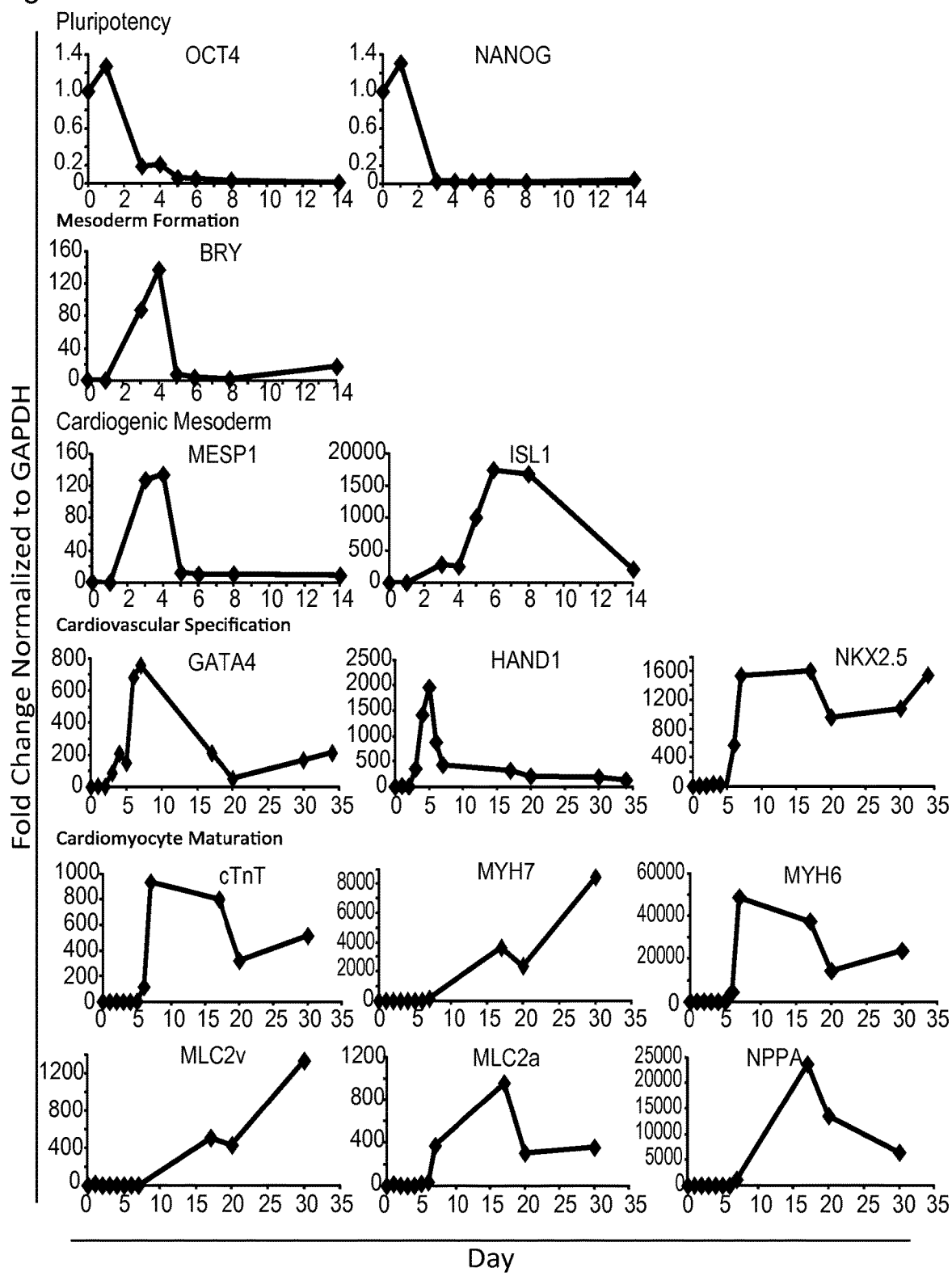
FIG. 2. Quantitative PCR-based gene expression analysis of EBs at different stages of cardiac differentiation. HES2 were subjected to the cardiac differentiation protocol described in FIG. 1. Expression levels of pluripotent, cardiac mesoderm markers, and cardiac specific genes were normalized and expressed relative to housekeeping gene GADPH. Plots shown are representative of three independent experiments.
Figure 3:
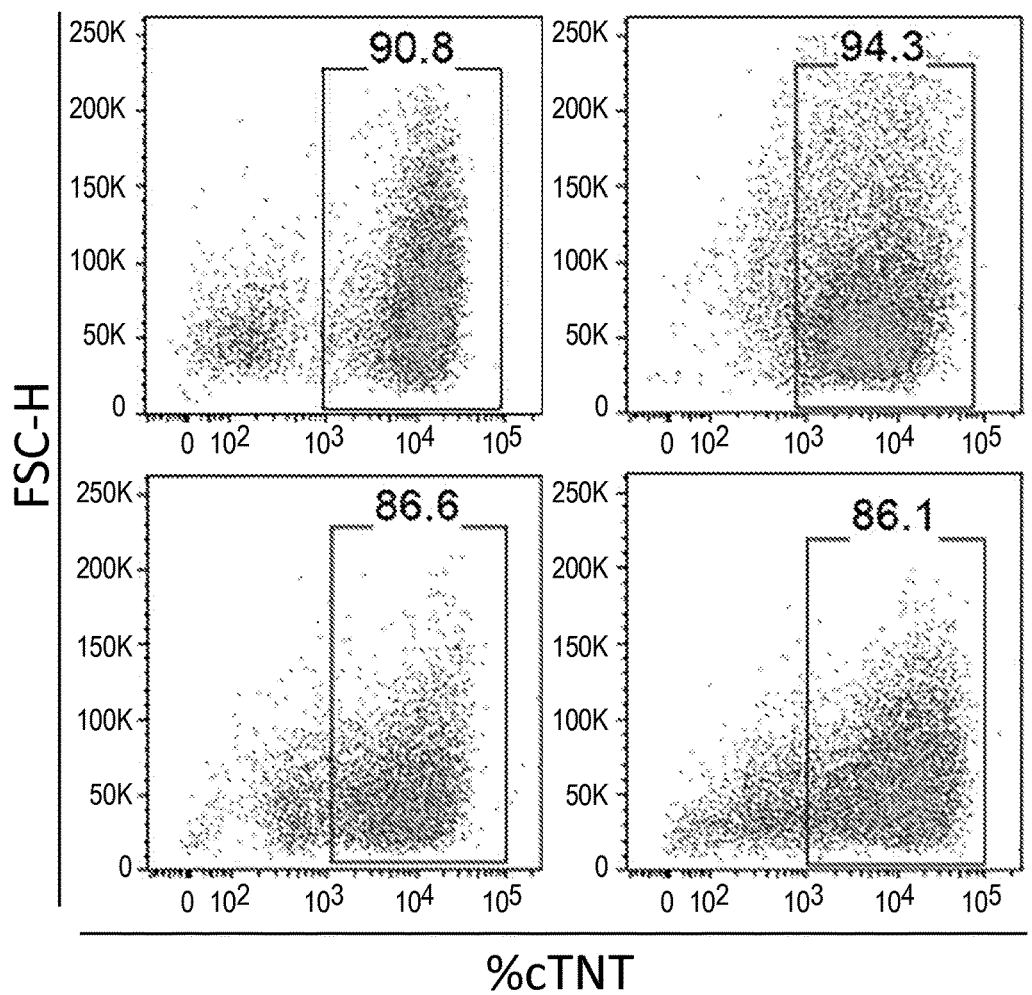
FIG. 3. Specification of cardiac differentiation in multiple hPSC lines. (A) Representative flow cytometry plots of cTNT+ cells differentiated from hPSCs. The entire well of one 6-well plate was enzymatically digested into a single cell suspension and 100,000 cells were analyzed. (B) Percentages of cTnT+ cells in day 16-18 EBs of HES2, H7, H9 and two non-viral PB and CB CD34+-derived hiPSC lines (iPS-PB2 and iPS-CB80). Mean±SEM.
Figure 3:
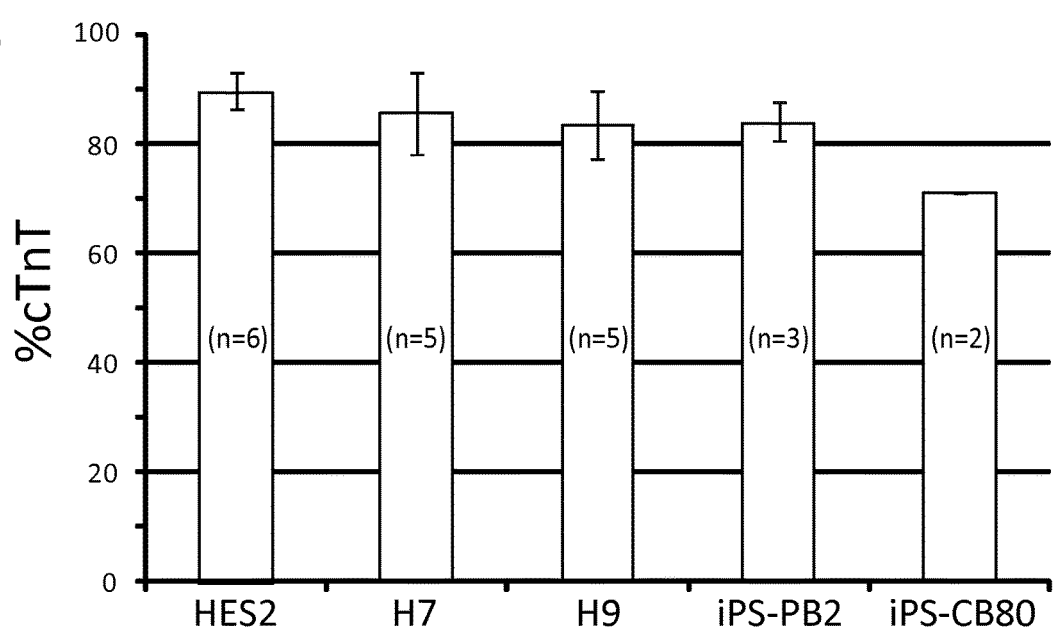
Figure 4:
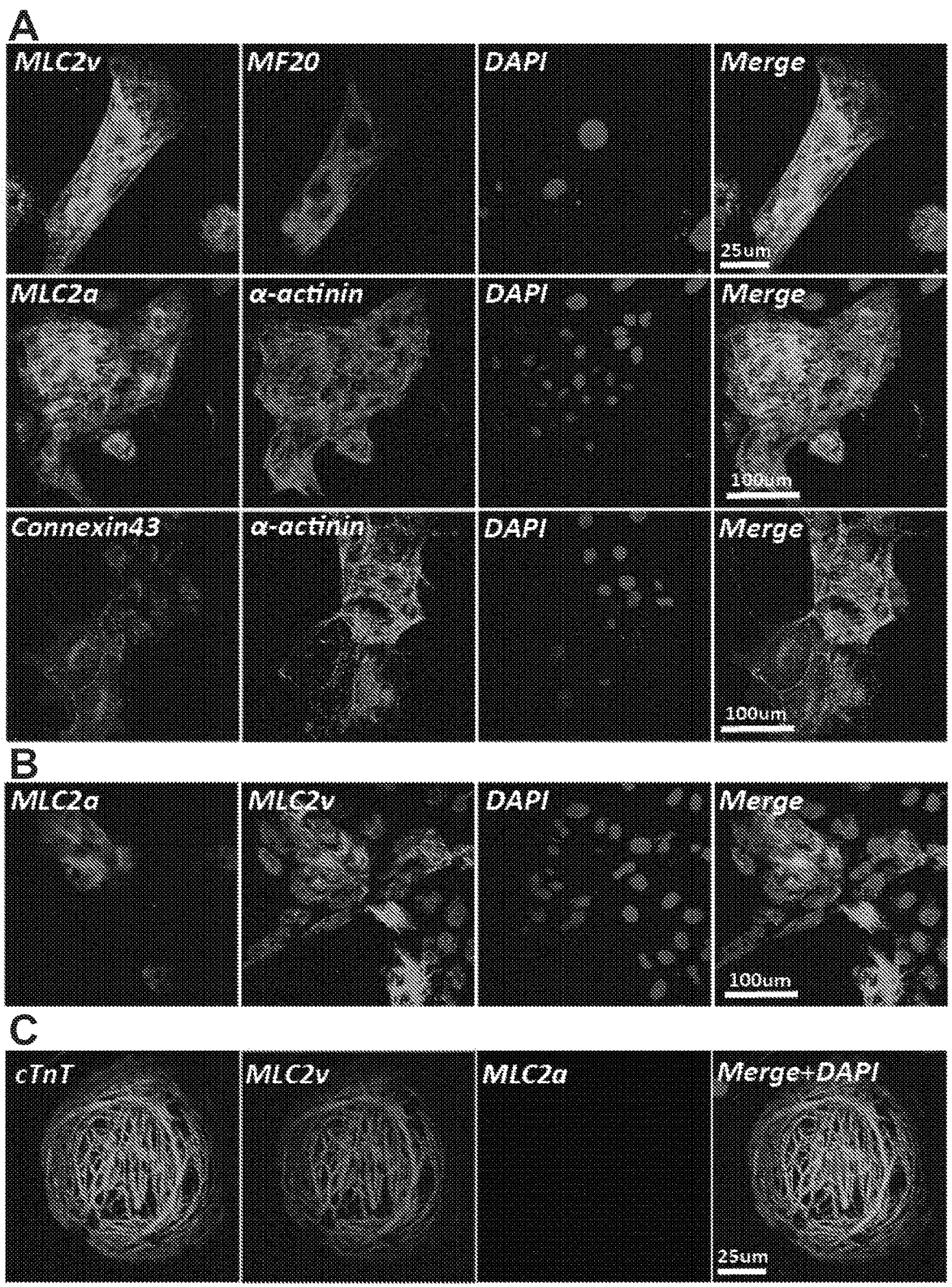
FIG. 4. Structural characterization of HES2-CM by immunostaining. (A) HES2-EB were digested into single cells at day 20 of differentiation, then co-stained for MLC2v/MF20, MLC2a/α-actinin, and Connexin43/α-actinin. Nuclei were counterstained with DAPI (blue). Representative immunostaining images for MLC2a and MLC2v in HES2-CMs examined at (B) day 20 and (C) day 40 post differentiation.
Figure 5:
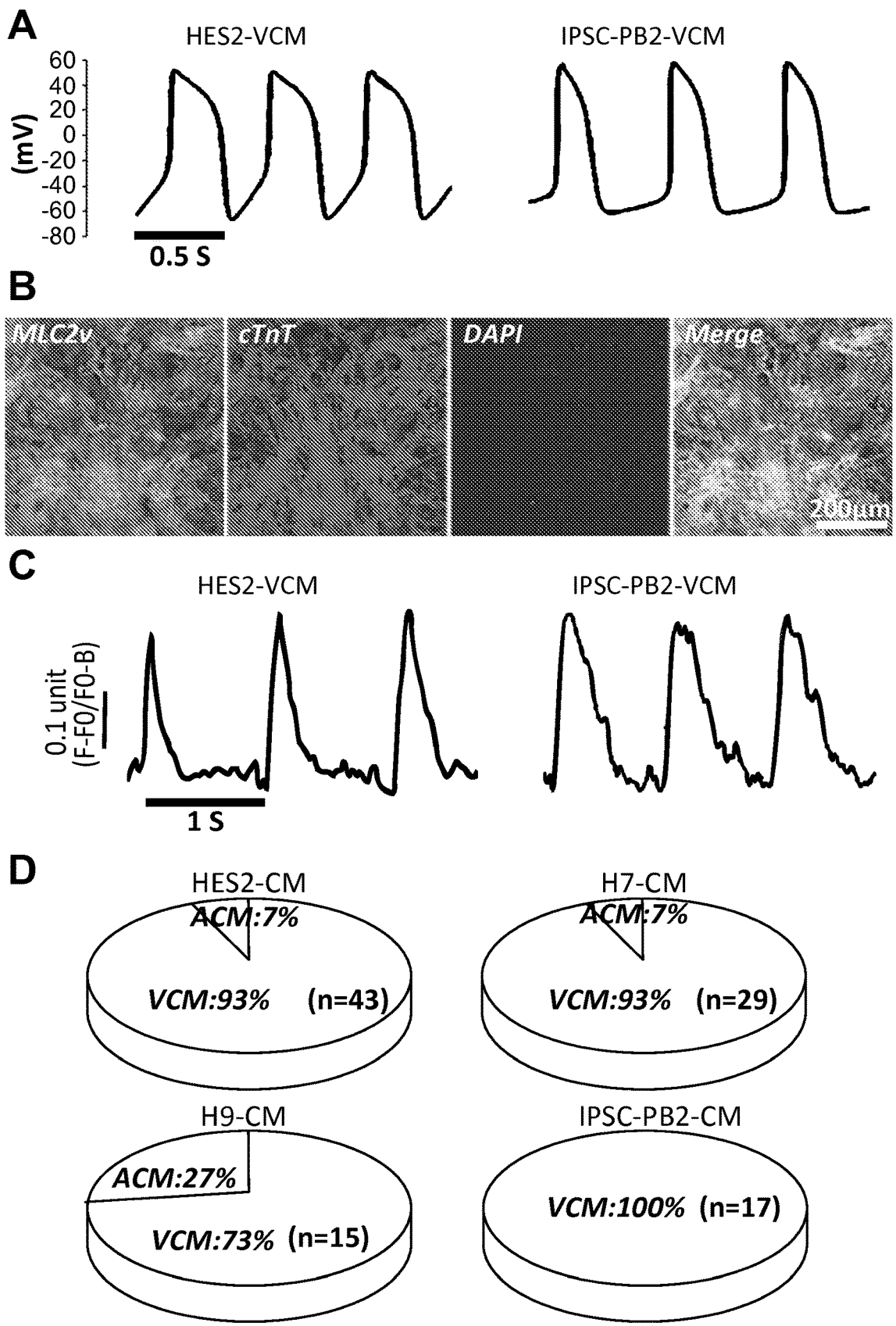
FIG. 5. Specification of ventricular differentiation of hPSCs. (A) Representative action potential profiles of HES2-VCMs and iPSC-PB2-VCMs measured by patch-clamp recordings. (B) Immunostaining of non-selected HES2-CMs for MLC2v and cTnT expression. HES2-EBs were digested into single cells then reseeded for immunostaining without any purification. Scale bar=200 μm. (C) Representative $Ca^{2+}$ transient tracings of HES2-VCMs and PB CD34+-derived iPSC-(iPSC-PB2)-VCMs paced by electrical field stimulation (1 Hz, 40 V/cm). All cells examined were >35 days old. (D) Percentages of cells expressing ventricular-type (VCM) and atrial-type (ACM) AP profiles detected by patch-clamping analyses.

The two-step method is highly efficient with about 90%, and typically greater than 90%, of the resulting population expressing the cardiomyocyte specific markers TNNT2, ACTN2 and MLC2v (FIG. 2). The enhanced differentiation efficiency of the protocol disclosed herein was confirmed in two additional hESC lines (H7 and H1), as shown in FIG. 14 and described in the following examples. Additional confirmation was obtained in an experiment demonstrating the effect of the protocol on a patient-specific induced pluripotent stem cell (iPSC) line, as disclosed in the examples. The cardiomyocytes produced by this method display characteristics of ventricular cardiac lineage cells, including the appropriate electrophysiological phenotype (FIGS. 3, 4, as well as Tables 1 and 6) and gene expression profile (FIG. 1), as well as organized sarcomeric structures (FIG. 3). In addition, ventricular cardiomyocytes displayed the expected electrophysiological and functional $Ca^{2+}$-handling characteristics (FIG. 4). The differentiated cells also exhibited physiological responses to cardioactive compounds (FIG. 5).

The use of small molecules in the generation of specialized cell populations under defined conditions in vitro also provides a chemical genetics-based interrogation of signaling pathway functions during cardiogenesis that bypasses the limitations of genetic approaches. The timely inhibition of the Wnt/β-catenin pathway by the small molecule IWR-1 reduced the heterogeneity of the hESC-derived cardiomyocytes, generating a homogeneous ventricular-like cardiomyocyte population. The delineation of the Wnt/β-catenin signaling pathway during cardiogenesis with small molecules, such as IWR-1, provides important insights into the molecular mechanisms that regulate cardiomyocyte subtype specification during development in the heart, such as in the human heart.

Apparent from the foregoing discussion is that the development of a fully chemically defined directed differentiation protocol also provides a powerful tool in understanding cardiac development. The generation and characterization of specific, pure cell populations during stages of the differentiation process and the subsequent exposure to small molecules has helped to elucidate vital aspects of the cellular pathways affected in cardiac development.[13] For example, the Wnt/β-catenin pathway is key in cardiac differentiation and development.[36-38] The differentiation system disclosed herein also provides an experimental platform for large-scale pharmacological screening, as well as providing a valuable source of cardiomyocytes for cell replacement therapies.

The differentiation system disclosed herein provides a reproducible and efficient experimental platform that advances our understanding and control of basic developmental processes, leading to uses and methods for preventing or treating a variety of cardiovascular diseases, disorders or conditions in humans and other animals, as well as facilitating large-scale pharmacological screening and providing a valuable and renewable source of ventricular cardiomyocytes for cell replacement therapies.

The following examples illustrate embodiments of the disclosure. Example 1 discloses materials and methods used in the studies disclosed herein, along with some data providing fundamental characterization of the differentiation protocol and system. Example 2 provides an exemplary implementation of the differentiation protocol to direct differentiation of hESCs into ventricular cardiomyocytes. Example 3 describes the phenotypic characteristics of the differentiated ventricular cardiomyocytes. Example 4 provides the electrophysiological characterization of the differentiated ciVCMs, and Example 5 provides a functional characterization of the differentiated ciVCMs. Finally, Example 6 shows the chronotropic responses of the differentiated ciVCMs to pharmacological compounds.

Example 1

Materials and Methods
Human Embryonic Stem Cell (hESC) and Induced Pluripotent Stem Cell Cultures All experiments used cells, such as the human embryonic stem cell lines, HES-2 (E502), H7 (WA07) and H1 (WA01), that were derived from the HES2 hESC line (Wicell, Madison, Wis.) propagated in feeder-free culture as previously described.[39] The iPSC line (SKiPS-33.1) was derived by the reprogramming of human dermal fibroblast obtained from a skin biopsy of a 45-year-old volunteer with informed consent (Staten Island Hospital) as described.[41] Briefly, the hESCs were maintained in an undifferentiated state on hESC-qualified Matrigel (BD Biosciences, San Jose, Calif.) in mTeSR™ 1 medium (Stem Cell Technologies, Vancouver, BC) at 37° C. in 5% $CO_2$, 90% $N_2$ and expanded following enzymatic treatment with dispase (Stem Cell Technologies, Vancouver, BC).

In addition, human induced pluripotent stem cell (hiPSC) lines were derived from neonatal CB $CD34^+$ or adult PB $CD34^+$ cells using the non-integrated episomal vectors, pCXLE-hOCT3/4-shp53, pCXLE-hSK, and pCXLE-hUL (Addgene).[63] Briefly, human CB and PB $CD34^+$ cells were purified (>95% purity) from anonymous donors and expanded in StemSpan™ H3000 (STEMCELL Technologies) with the cytokine cocktail CC100 (STEMCELL Technologies) for 3 days. Cells were nucleofected with the episomal vectors in the human CD34 cell solution nucleofector kit (Amaxa) according to the manufacturer's protocol. After 72 hours, cells were transferred to Matrigel™ (BD Biosciences)-coated plates in mTeSR™ 1 medium. Morphological changes were observed a few days later. Colonies resembling hPSCs typically started to appear on day 7, and were picked on day 13 after nucleofection. hESC, H7 and H9 (WiCell) and HES2 (ESI) (passages 35 to 55) and hiPSC lines were maintained in feeder- and serum-free condition in mTeSR™ 1 medium (STEMCELL Technologies) on Matrigel at 37° C. in 5% $CO_2$ in a humidified normoxic environment.

hiPSC Validation

To characterize hiPSC clones, cultured cells were fixed by 4% paraformaldehyde in PBS for 15 minutes, followed by permeabilization by 0.1% Triton X-100 for 15 minutes, and washing with PBS for 3 times. The fixed samples were stained with anti-OCT4, SSEA-4, Tra-1-81 for 2 hours at room temperature, then with fluorochrome-conjugated goat anti-rabbit or anti-mouse secondary antibodies for 1 hour. Antibodies used in characterizing cells are provided in Table 1. To test for pluripotency, hiPSCs were differentiated to form EBs in DMEM/F12 (Life Technologies) with 20% KNOCKOUT Serum Replacement (KSR) (Life Technologies), 2 mM nonessential amino acids, 2 mM L-glutamine, 0.1 mM β-mercaptoethanol. At day 15, EBs were stained for markers of the three germ layer (i.e., Tuji, SMA and AFP). For teratoma formation, $1 \times 10^6$ iPSCs were injected subcutaneously into NOD/SCID immunodeficient mice. Teratomas were harvested and stained 7-9 weeks after injection for Hematoxylin and Eosin (H&E) staining. Karyotyping was done according to a published protocol.[64]

TABLE 1

Antibodies Used For Characterizing hPSCs and hPSCs-CMs.

| Antibody list | Isotype/source/clone | Concentration |
|---|---|---|
| Primary antibodies | | |
| AFP | Mouse IgG2a/Sigma/C3 | 1:250 |
| Cardiac troponin T (for flow cytometry) | Mouse IgG1/Abcam/1C11 | 1:200 |
| Cardiac troponin T (for immunostaining) | Mouse IgG1/Lab vision/13-11 | 1:200 |
| Ki67 | Mouse IgG1/Biolegend/Ki-67 | 1:200 |
| Connexin 43 | Mouse IgG1/Abcam/GJA1 | 1:200 |
| COXIV | Rabbit IgG1/Abcam/Ab16056 | 1:200 |
| MF20 | Mouse IgG2b/DSHB/MF20 | 1:20 |
| MLV2a | Mouse IgG2b/Sysy/56F5 | 1:200 |
| MLC2v | Rabbit polyclonal/ProteinTech | 1:200 |
| OCT4 | Rabbit polyclonal/Santa Cruz/C-10 | 1:200 |
| Sarcomeric α-actinin | Mouse IgG1/Abcam/EA-53 | 1:200 |
| SMA | Mouse IgG2a/Sigma/1A4 | 1:400 |
| SSEA-4 | Mouse IgG3/DSHB | 1:200 |
| Tra-1-81 | Mouse IgM/Millipore/Tra-1-81 | 1:100 |
| TUJ1 | Mouse IgG1/Millipore/TU20 | 1:250 |
| Secondary antibodies | AF488 anti-mouse IgG/Invitrogen | 1:200 |
| | AF488 anti-mouse IgM/Invitrogen | 1:200 |
| | AF488 anti-rabbit IgG/Invitrogen | 1:200 |
| | AF594 anti-mouse IgG2a/Invitrogen | 1:200 |
| | AF647 anti-mouse IgG2a/Invitrogen | 1:200 |
| | AF647 anti-rabbit IgG/Invitrogen | 1:200 |
| | FITC anti-mouse IgG2a/Biolegend | 1:200 |

TABLE 1-continued

Antibodies Used For Characterizing hPSCs and hPSCs-CMs.

| Antibody list | Isotype/source/clone | Concentration |
|---|---|---|
| | FITC anti-mouse IgG2b/Biolegend | 1:200 |
| | PE anti-mouse IgG1/Biolegend | 1:200 |
| | PE-Goat anti-mouse IgG3/Santa Cruz | 1:200 |

Tissue Collection and Histological Analysis

Kidney specimens were embedded in paraffin and sectioned at 5 µm on a cryostat. Sections were then deparaffinized and rehydrated through a graded concentrations of alcohol. Antigen retrieval was done by treating tissues sections with 10 mM sodium citrate buffer (0.05% Tween 20, pH 6.0; TBS) in a microwave oven for 30 minutes. Sections were next rinsed with cold water, followed by blocking, then incubating with anti-cTNT Antibody overnight at 4° C. After washing, 0.3% hydrogen peroxide in TBS was used to block endogenous peroxidase activity. Labeled polymer goat anti-mouse immunoglobulins conjugated to horseradish peroxidase (Dako Corporation, USA) was added for 30 minutes, followed by DAB+ Substrate-Chromogen solution for 5 minutes. All stained sections were counterstained with Mayer's hematoxylin, dehydrated in graded alcohol and mounted. Sections were examined using an Axiophot microscope (Carl Zeiss). For control, isotype antibodies were used to examine the level of non-specific staining.

Cardiac Differentiation

For directed cell differentiation, undifferentiated hPSCs were digested into smaller clusters using Dispase (STEMCELL Technologies; 1 mg/ml for 8 minutes at 37° C.) and seeded onto Matrigel™-coated plates at $3 \times 10^4$ cells/ml in mTeSR™ 1 medium for 4 days until there was about 80-90% confluence on D0. To initiate cardiac differentiation, hPSCs were digested into single cell suspensions using Accutase (Invitrogen) and cultured in mTeSR™ 1 medium with Matrigel™ (40 µg/ml) with BMP-4 (1 ng/ml, Invitrogen) and Rho kinase inhibitor (ROCK) Inhibitor (10 µM; R&D) under a hypoxic condition with 5% $O_2$. Twenty-four hours later, the culture was washed and replaced in StemPro34 SFM (Invitrogen) with ascorbic acid (AA, 50 µg/ml; Sigma), 2 mM GlutaMAX-1 (Invitrogen), BMP4 (10 ng/ml) and human recombinant activin-A (10 ng/ml; Invitrogen) for 3 days. On day 4, IWR-1, a Wnt inhibitor, (5 µM; Enzo Life Sciences) was added. Cardiac mesodermal cells developed into functional contracting clusters could be detected as early as day 8. On day 8, cells were transferred to a normoxic environment and maintained in StemPro34 SFM+AA medium for further characterization. In some cases, the cardiac mixtures (30-50 day old) were transduced with the recombinant lentivirus (LV)-MLC2v-Tdtomato-T2A-Zeo. MLC2v-positive cells were selected using the antibiotic Zeocin.

Immunostaining

For immunostaining of cardiac cells, beating clusters (between 16-35 days of differentiation) were dispersed into single cells, e.g., by trypsinization (0.04% Trypsin/0.03% EDTA Solution; Promocell) for 15 minutes at 37° C. Dispersed cells were immunostained with anti-cTnT, sarcomeric, α-actinin, connexin 43, COXIV, myosin heavy chain (MF20), two isoforms of myosin light chain 2, MLC2a and MLC2v antibodies listed in Table 1. Primary antibodies were diluted in PBS with 1% BSA and incubated at room temperature (RT) for two hours. Alexa Fluor (AF)488-conjugated goat anti-mouse IgG or AF555 anti-mouse IgG (Invitrogen) were used as secondary antibodies and stained for 1 hour at RT. Coverslips were mounted onto glass slides in Prolong Gold mounting medium with DAPI (Invitrogen) and samples were imaged on a LSM Carl Zeiss 510 Meta (Carl Zeiss, Germany) or a Nikon Eclipse TiS microscope. For flow cytometry, cells were digested and resuspended in PBS with 2% FBS. To stain for intracellular markers, cells were fixed, permeabilized and stained with antibodies against various cardiac markers. To measure cardiac differentiation, percentages of CM were estimated based on the % of cTnT-positive cells at differentiation day 16-18.

Metabolic Stress and Mitochondrial Membrane Potential

Mitochondrial membrane potential in HES2-VCMs was measured with the potential-sensitive dye JC-1 (Invitrogen). LV-MLC2v-Tdtomato-T2A-Zeo transduced and Zeo-selected HES2-VCMs (30- to 50-day-old) were incubated at 37° C. with 0.5 µM JC-1 in serum free DMEM medium for 15 minutes. To simulate metabolic oxidative stress, hES2-VCMs were treated with hydrogen peroxide ($H_2O_2$; 100 µM) for 30 minutes at 37° C., after which JC-1 orange and green fluorescence intensities were measured for mitochondrial membrane potential with a LSM Carl Zeiss 510 Meta microscope.

Mitochondrial Volume Estimation

HES2-VCMs were incubated at 37° C. with 0.1 µM MitoTracker Deep Red and 0.1 µM Cell Tracker (Invitrogen) for 30 minutes for mitochondrial volume estimation. Stack images of mitochondria and cytoplasm were obtained with LSM Carl Zeiss 510 Meta. 3D images of HES2-VCMs were constructed and mitochondrial volume estimated as % of total cell volume with the imaging analysis software Imaris (Bitplane, St. Paul, Minn.).

RNA Extraction, cDNA Synthesis, and Gene Expression Analysis by Real-Time PCR

Relative gene expression was determined using two-step quantitative real-time PCR. Total RNA was isolated with the RNeasy Isolation kit (Qiagen, Valencia, Calif.) with on-column DNase I treatment to eliminate contaminating genomic DNA using RNase-free DNase Set (Qiagen, Valencia, Calif.) according to the manufacturer's instructions. About 1 µg total RNA from each sample was reverse-transcribed using the SuperScript® VILO™ cDNA Synthesis Kit (Invitrogen, Carlsbad, Calif.) according to the manufacturer's protocol. Quantitative RT-PCR reactions were performed with iTaq Fast SYBR Green Supermix (Bio-Rad, Hercules, Calif.) on an ABI Prism 7500 Real Time PCR System using standard parameters. The primer sets used in this study are listed in Table 2. For each set of primers, a no-template control and a no-reverse-amplification control were included. Post-amplification dissociation curves were performed to verify the presence of a single amplification product and the absence of primer-dimers. Fold changes in gene expression were determined using the comparative $C_T$ method (ΔΔCt) with normalization to the B2M housekeeping gene as an endogenous control.

TABLE 2

Real Time qPCR sequences

| Gene | Forward Sequence (5' → 3') | Sequence Identifier (SEQ ID NO) | Reverse Sequence (5' → 3') | Sequence Identifier (SEQ ID NO) |
|---|---|---|---|---|
| ISL1 | GCAGAGTGACATAGATCAGCCTG | 1 | GCCTCAATAGGACTGGCTACCA | 2 |
| BRY | GCTGTGACAGGTACCCAACC | 3 | CATGCAGGTGAGTTGTCAGAA | 4 |
| HAND1 | CAAGGATGCACAGTCTGGCGAT | 5 | GCAGGAGGAAAACCTTCGTGCT | 6 |
| CTNT | AAGAGGCAGACTGAGCGGGAAA | 7 | AGATGCTCTGCCACAGCTCCTT | 8 |
| NKX2.5 | CACCTCAACAGCTCCCTGAC | 9 | AATGCAAAATCCAGGGGACT | 10 |
| MESP1 | CTGTTGGAGACCTGGATGC | 11 | CGTCAGTTGTCCCTTGTCAC | 12 |
| GATA4 | GCAGCCAGAGTCCCTCAG | 13 | CTGGCTTTTTGCCTCCTG | 14 |
| TBX5 | CGATTCGAAACCCGAGAG | 15 | GAAACACTTTGATTCCCTCCA | 16 |
| MYL2 | GCAGGCGGAGAGGTTTTC | 17 | AGTTGCCAGTCACGTCAGG | 18 |
| FLK1 | GGAACCTCACTATCCGCAGAGT | 19 | CCAAGTTCGTCTTTTCCTGGGC | 20 |
| SMMHC | GTCCAGGAGATGAGGCAGAAAC | 21 | GTCTGCGTTCTCTTTCTCCAGC | 22 |
| MIXL1 | CCCGACATCCACTTGCGCGAG | 23 | GGAAGGATTTCCCACTCTGACG | 24 |
| B2M | GGGATCGAGACATGTAAGCAG | 25 | CAAGCAAGCAGAATTTGGAA | 26 |
| OCT4 | CCTCACTTCACTGCACTGTA | 27 | CAGGTTTTGTTTCCCTAGCT | 28 |
| NANOG | CTCCAACATCCTGAACCTCAGC | 29 | CGTCACACCATTGCTATTCTTCG | 30 |
| BYR | TGAGCCTCGAATCCACATAGTG | 31 | AAGCAGTCACCGCTATGAAC | 32 |
| HAND1-B | CCACCCTTTTGGAGCGAATT | 33 | AATTAGAGAAGACGGCGTCGG | 34 |
| MLC2a | CAGGCCCAACGTGGTTCTT | 35 | CCATCACGATTCTGGTCGATAC | 36 |
| MLC2v | CCTTGGGCGAGTGAACGT | 37 | GGGTCCGCTCCCTTAAGTTT | 38 |
| MYH6 | CAGCACAGAGCTCTTCAAGC | 39 | GTCCGAGATTTCCTCCTGAA | 40 |
| MYH7 | GAGACTGTCGTGGGCTTGTA | 41 | CTTCTCAATAGGCGCATCAG | 42 |
| NPPA | ATGAGCTCCTTCTCCACCAC | 43 | TCCAGCAAATTCTTGAAATCC | 44 |
| GAPDH | GAAATCCCATCACCATCTTCCAGG | 45 | GAGCCCCAGCCTTCTCCAGT | 46 |

Total RNA was extracted from samples using the RNeasy Mini Kit (Qiagen) following DNase I (Promega) treatment for the removal of potentially contaminating genomic DNA. cDNA was prepared using the QuantiTect Rev. Transcription Kit (Qiagen) following the manufacturer's protocol. Gene expressions were quantified using the StepOnePlus™ Real-Time PCR system (Applied Biosystems). PCR amplification was carried out in 96-well optical plates consisting of 100 ng of cDNA template, 5 pmol each of forward and reverse primers, and 1× KAPA SYBR® Fast qPCR Master Mix (KAPA Biosystems). The reactions were incubated at 95° C. for 3 minutes, and followed by 40 cycles of 95° C. for 3 seconds, and 60° C. for 20 seconds. GAPDH was used as an internal control to normalize loading and all reactions were performed in triplicate. Primers are listed in the sequence listing and in Table 2.

Genetic Labeling of hESC-Derived Ventricular Cardiomyocytes

Single cells were isolated from cardiogenic EBs and were plated at low density on a Matrigel-coated coverslip and cultured at 37° C., 5% $CO_2$/20% $O_2$ with the medium containing 80% DMEM, 20% FBS defined (HyClone), 1 mM L-glutamine, 1% NEAA. The next day, cells were transduced with recombinant lentiviral vector in which the short fragment (250 base pairs) of the human myosin light chain (MLC)-2v promoter drove the expression of tdTomato (LV-MLC2v-tdTomato; MOI=5) 12. Subsequent functional assays were performed on 7-15 days post-transduction at physiological temperature.

Action Potential (AP) Characterization

Action potentials (APs) of chemically induced ventricular cardiomyocytes (ciVCMs) were recorded using the whole-cell configuration of the patch-clamp technique (HEKA Instruments Inc. Southboro, Mass., USA) at 37° C. The voltage-clamp mode was employed with cell capacitance and series resistance (≥70%) on-line compensated. The current-clamp mode with 100-1000 pA pulse of 5 ms delivered to the cells was employed with cell capacitance and series resistance (≥70%) on-line compensated. AP parameters such as the resting membrane potential (RMP), upstroke velocity and AP duration were analyzed as described.[40, 44] Patch pipettes were prepared from 1.5 mm thin-walled borosilicate glass capillaries using a Sutter micropipette puller P-97, and had typical resistance of 4-6 MΩ with an internal solution containing (in mM): 110 K-aspartate, 20 KCl, 1 $MgCl_2$, 0.1 Na-GTP, 5 Mg-ATP, 5

Na$_2$-phosphocreatine, 1 EGTA, 10 HEPES, pH adjusted to 7.3 with KOH. The composition of external Tyrode's solution (in mM): 140 NaCl, 5 KCl, 1 CaCl$_2$, 1 MgCl$_2$, 10 glucose, 10 HEPES, pH adjusted to 7.4 with NaOH.

In accordance with the electrophysiological and pharmacological protocols used in voltage clamp experiments disclosed herein, action potential determinations involved the use of the same internal and external solutions as those used for manual patch clamp experiments. Additionally, the sealing solution for all ion channel recordings contained: 150 mM NaCl, 4 mM KCl, 1.2 mM CaCl$_2$, 1 mM MgCl$_2$, and 10 mM HEPES, pH 7.4. For 3. L-type Ca2+ currents (I Ca, L), the internal solution contained: 145 mM CsCl, 5 mM NaCl, 2 mM CaCl$_2$, 5 mM MgATP, 10 mM HEPES and 5 mM EGTA, with pH being adjusted to 7.2 with CsOH. The external solution contained: 160 mM TEA-Cl, 1 mM MgCl$_2$, 5 mM CaCl$_2$, 10 mM Glucose and 10 mM HEPES, pH 7.4, with. 0.01 mM TTX and 2 mM 4-AP being added during the recording. Cells were held at −60 mV and pulsed from −50 to 60 mV at 10 mV increments. For I Na, the internal solution contained: 135 mM CsCl, 10 mM NaCl, 2 mM CaCl$_2$, 5 mM MgATP, 5 mM EGTA, and 10 mM HEPES, pH 7.2. The external solution contained 110 mM K-aspartate, 50 mM NaCl, 1.8 mM CaCl$_2$, 1 mM MgCl$_2$, 10 mM D-Glucose, 10 mM HEPES and 0.001 mM Nifedipine. The pH was adjusted to 7.2 with CsOH. Cells were held at −60 mV and pulsed from −120 to 50 mV at 10 mV increments. For I Kr, the internal solution contained 110 mM K-aspartate, 20 mM KCl, 5 mM MgATP, 1 mM EGTA, 1 mM MgCl$_2$, and 10 mM HEPES, 5 mM Na$_2$-phosphocreatine, 0.1 mM NaGTP, pH 7.4 titrated with KOH. The external bath solution contained 140 mM KCl, 15 mM NaCl, 10 mM glucose, 1 mM MgCl$_2$, 1.2 mM CaCl$_2$, 0.002 mM Nifedipine and 10 mM HEPES, pH 7.4 titrated with NaOH. Cells were held at −60 mV and pulsed from −160 to 60 mV at 10 mV increments for 500 ms. The current was defined as E4031-sensitive (1 μM).

The electrophysiological experiments disclosed in the Examples were performed using the whole-cell patch-clamp technique as previously described.[65-67] To profile chamber-specific subtypes of the hPSC-CMs, action potentials of the myocytes were randomly probed at 37° C. with the patch-clamp technique using an EPC-10 amplifier and Pulse software (Heka Elektronik, Germany), with the current-clamp mode (0.1-0.5 nA for 1-5 ms) under the whole-cell configuration applied. The hPSC-CMs were categorized into nodal-, atrial- or ventricular-like, as previously described.[62, 65, 66] Voltage-clamp recordings of ionic currents were performed using an automated parallel patch-clamp system (PatchXpress 7000A, Molecular Devices) using standard electrophysiological and pharmacological protocols for isolating the ionic component of interest.

Confocal Ca$^{2+}$ Imaging

Intracellular Ca$^{2+}$ ([Ca$^{2+}$]i) transients were imaged by a spinning disc laser confocal microscope (PerkinElmer) on hPSC-CMs loaded with 1.5 μM X-Rhod-1 (Invitrogen) as previously described[66]. After dye loading, experiments were performed at 37° C. in Tyrode's solution containing: 140 mM NaCl, 5 mM KCl, 1 mM MgCl$_2$, 1.25 mM CaCl$_2$, 10 mM HEPES and 10 mM D-glucose at pH 7.4. Electric pulses (40 ms pulse duration; 40 V/cm; 1 Hz) generated by a field generator were continuously applied to pace electrically induced Ca$^{2+}$ transients (E[Ca$^{2+}$]i). The amplitudes of E[Ca$^{2+}$]i are presented as the background corrected pseudo ratio ($\Delta F/F$)=(F−F$_{base}$)/(F$_{base}$−B) where F$_{base}$ and F is the measured fluorescence intensity before and after stimulation, respectively, and B is the average background signal from areas adjacent to the targeted cell. The transients rise (V$_{upstroke}$) and the transients decay (V$_{decay}$) were subsequently calculated and analyzed.

Transplantation and In Vivo Tracking of hESC-VCM

H9$^{DF}$ cells stably expressing a double-fusion reporter gene consisting of firefly luciferase and enhanced GFP[23,24] were used for in vivo monitoring of CM survival. Specifically, 2-3×10$^5$ H9$^{DF}$-CM were transplanted to the kidney capsule of NOD.Cg-Prkdc$^{scid}$Il2rg$^{tm1Wjl}$/SzJ mice (Jackson, USA) (6-10 weeks old). Transplanted cell survival was longitudinally monitored via bioluminescence intensity image (BLI) using the Xenogen in vivo imaging system (Caliper Life Sciences). Briefly, mice were anesthetized with isoflurane and D-Luciferin (Invitrogen) was administrated intraperitoneally at a dose of 375 mg/kg of body weight. BLI signal was measured in maximum photons per sec per centimeter square per steradian (p/s/cm$^2$/sr). For detection of the transplanted CM, animals were killed at different time points and kidneys were harvested and stained for the presence of cTnT-positive cells (see Example 1 for details).

Microelectrode Array Recordings

A high-resolution microelectrode array recording system (Multichannel Systems, Reutlingen, Germany) was used to characterize the electrophysiological properties of hESC-derived cardiomyocytes.[33] At day 21 post-differentiation, cardiogenic EBs or cardiomyocytes were plated on fibronectin-coated microelectrode array plates that consisted of a 50×50 mm glass substrate with an embedded 1.4×1.4 mm matrix of 60 titanium nitride-gold contact electrodes with an inter-electrode distance of 200 μm. The extracellular field potentials (FP) were recorded simultaneously from all 60 electrodes and then band-pass-filtered from 1 to 10 kHz. Recordings were performed in serum-free culture medium at 37° C. Following baseline recordings, escalating doses of isoproterenol (10$^{-9}$ mol/l to 10$^{-6}$ mol/l; or sotalol (10$^{-9}$ mol/l to 10$^{-5}$ mol/l; Sigma, St Louis, Mo.) were tested. The solution was static during the recording period and the temperature was kept at 37° C. Data were analyzed off-line to determine interspike interval, FP max (peak-to-peak amplitude) and FP min using the MC_Rack data analysis software according to manufacturer's instructions (Multi-Channel Systems, Reutlingen, Germany).

Optical Mapping

CiVCMs were plated on Matrigel-coated coverslips for 72 hours to allow establishment of intercellular electrical junctions. The cells were loaded with 2 mM di-4-ANEPPS (Invitrogen, Carlsbad, Calif.) for 10 minutes at room temperature in Tyrode's solution, consisted of (mM) 140 NaCl, 5 KCl, 1 MgCl$_2$, 1 CaCl$_2$, 10 glucose, and 10 HEPES at pH 7.4. A halogen light filtered by a 515±35 nm band-pass filter excited the voltage-sensitive dye. The emission was filtered by a 590 nm long-pass filter. AP conduction through a hESC-CM monolayer was measured using MiCam Ultima optical mapping system (SciMedia) with a 1× objective and 1× condensing lens to yield a 10×10 mm$^2$ field-of-view. A co-axial point stimulation electrode at 1.5 Hz, 8 V, and 10 ms pulse duration stimulated the cells. Data were collected at room temperature with a sampling rate of 0.2 kHz and analyzed using BV Ana software (SciMedia).

Alternatively, at 21 to 25 days post-differentiation, cardiomyocyte monolayers were prepared by plating single-cell preparations on matrigel-coated coverslips at a density of 10$^5$ cells per cm$^2$. After 96 hours, the cells were incubated with the voltage-sensitive dye di-4-ANEPPS (2 mM) (Invitrogen, Carlsbad, Calif.) for 10 minutes at room temperature in Tyrode's solution. The cells were stimulated with co-axial point stimulation electrode (typically 1.5 Hz, 8 V/cm, 10 ms duration). Fluorescence images were acquired with the MiCam Ultima optical mapping system (SciMedia, Costa Mesa, Calif.) using a 1× objective and 1× condensing lens in a 10×10 mm$^2$ field-of-view. Optical mapping image processing and data analysis were again performed with the BV_Analyzer software (SciMedia, Costa Mesa, Calif.).

Statistical Analysis

Statistical significance was analyzed with the Student's unpaired t-test. The electrophysiology datasets were analyzed using the Kolmogorov-Smirnov test. P<0.05 was considered significant.

Example 2

Direct Differentiation of hESCs Toward Ventricular Cardiomyocytes

Figure 9:
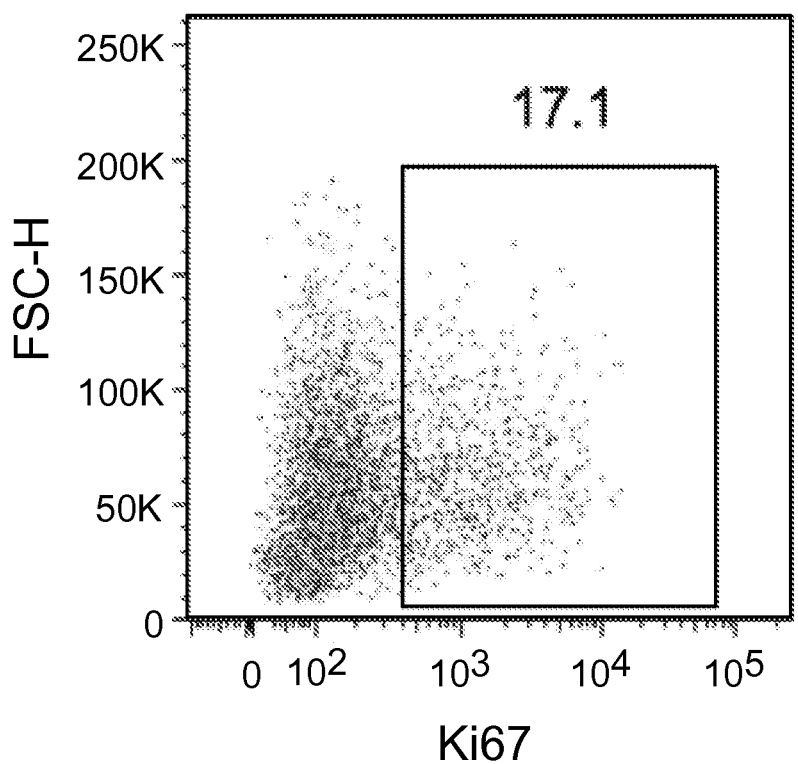
FIG. 9. Proliferation of HES2-CMs. HES2 cells were differentiated to CMs as described in the Materials and Methods. At day 17 of differentiation, cardiogenic EB clusters were digested into single cells, then co-stained with anti-cTNT and Ki67 antibodies. A representative flow cytometry plot of Ki67 staining of gated cTNT+ cells is shown (n=2).

A method, or protocol, for efficiently directing human embryonic stem cells (hESCs) to differentiate into ventricular cardiomyocytes was developed. The method for ventricular specification is schematically summarized in FIG. 1A. To start, undifferentiated HES2 cells, a hPSC cell line, were seeded at 30,000 cells/cm$^2$ for expansion in mTeSR™ 1 medium for 4 days. On day 0, hPSCs were digested into single cells and cultured in suspension in mTeSR™ 1 medium with Matrigel™ along with BMP4 (1 ng/ml) and Rho kinase inhibitor (10 μM) to induce differentiation. After 24 hours, the media was changed to StemPro34 SFM with BMP4 (10 ng/ml), activin A (10 ng/ml) and ascorbic acid (50 μg/ml) to induce the formation of cardiogenic mesodermal embryoid bodies (EB). As the last step, on day 4 when nicely compact, rounded aggregates could be observed, IWR-1 (5 μM) was added to suppress Wnt signaling. As early as Day 8, greater than 70% hEBs from 30 out of 30 independent differentiation reactions became spontaneously contracting (compared to about 50% on day 10-12 of Keller[21]). On Day 16-18, about 100% hEBs were beating and for the cTnT-positive cells, about 17% were Ki67-positive proliferating (FIG. 9).

As anticipated, using real-time RT-PCR analysis, transcript expression of the pluripotency markers OCT4 and Nanog decreased time-dependently, and rapidly became undetectable by days 4-5 (FIG. 2). By contrast, the transcript expression of T-box factor Brachyury (T) and helix-loop-helix transcription factor mesoderm posterior 1 (MESP1), one of the earliest "cardiac" mesoderm markers, transiently spiked during days 2-5 upon the addition of BMP4 and activin A. During the same time interval, the cardiac progenitor marker Isl1 as well as the transcription factors GATA4 and Hand1, critical for early cardiac differentiation, were also expressed. The early cardiac-progenitor marker Nkx2.5 appeared shortly after on day 5 (after IWR addition), peaked at day 8 and continued to remain high beyond day 14. Consistent with successful cardiac differentiation, further analyses revealed that transcripts of sarcomeric proteins such as MYH6, MYH7, cTnT and NPPA, signatures of contractile cardiomyocytes (CMs), also had similar time-dependent expression patterns. Expression levels of ML2Cv, a marker of mature ventricular CM, increased to a high level at day 16 and remained at that level for over 30 days. By contrast, the expression of MLC2a, which is normally expressed in atrial and immature ventricular CM, peaked at day 16 and declined afterwards. The temporal transcript expression profiles of the various pluripotency, mesodermal and cardiac markers are summarized in FIG. 2.

Example 3 hESC-CM Displayed a Time-Dependent Switch from MLC2a to MLC2v-Positive

To quantitate the efficiency of the protocol, flow cytometry analysis was performed on differentiated HES2 cells collected at day 16-18. As depicted in FIG. 3A, the yield of cTnT$^+$ cells was 90.8% for the representative reaction shown, with an average of 87±3.4% for the HES2 line (n=6 independent reactions; FIG. 3B). Immunostaining experiments confirmed the subcellular expression of cardiac-specific proteins (i.e., MLC2v, MLC2a, MF20, α-actinin, and connexin 43) with the expected sarcomeric structures (FIG. 4A), indicating that the derived cells were hESC-CMs. As shown in FIG. 4B, by day 20, about 85% of the differentiated cells were positively stained for ML2Cv. Consistent with the qRT-PCR data, only about 35% of the MLC2v-positive cells were also positive for MLC2a (FIG. 4B). By day 40, essentially all of HES2-VCM did not express MLC2a but only MLC2v (FIG. 4C), indicating that the derived VCMs were capable of maturation in vitro. Considering the input of 300,000 hESCs at day −4, the output of the protocol, as determined by flow cytometry, was about 32-72 cTnT-positive cells per HES2 cell at day 14. Thus, the method, or protocol, disclosed herein as requiring fewer reagents and/or lower quantities of those reagents relative to other technologies for directing cell differentiation, is able to direct differentiation to cardiomyocytes, e.g., ventricular cardiomyocytes, in an efficient and robust manner.

Example 4

Electrophysiological Characterization of ciVCMs

Existing differentiation protocols generate a population of heterogeneous cardiomyocytes that are classified into atrial-, ventricular- and nodal-like subtypes based on their electrophysiological properties. The patch-clamp method was used to analyze the action potential (AP) and electrophysiological properties of the cardiomyocytes generated in the protocol disclosed herein. The AP waveforms were classified into atrial-, ventricular-, or nodal-like cell types based on the AP parameters (see Table 3 for a complete set of the criteria).

Table 3 discloses action potential (AP) parameters used for the classification of hESC-derived cardiomyocyte subtypes. The cardiomyocytes were categorized into nodal-, atrial-, or ventricular-like phenotypes, based on their electrophysiological properties, such as the APA (V), dV/dt (mV/ms), APD50 (ms) and APD90 (ms). The nodal-like AP subtype was assigned to cells that exhibited: i) a prominent phase-4 depolarization, ii) a slow upstroke (dV/dt), iii) a small APA, iv) relatively depolarized MDP and v) were spontaneously firing. The atrial- and ventricular-like types of action potentials differed by the shape of their plateau phases and the AP duration. The atrial-like are triangle-shaped with shorter AP durations than the ventricular-like cells. The ventricular-like exhibit more pronounced plateau phases and longer AP durations. APA: action potential amplitude; dV/dt: maximum upstroke velocity; APD90: action potential duration at 90% repolarization; APD50: action potential duration at 50% repolarization.

TABLE 3

| Subtype | APA (mV) | dV/dt (mV/ms) | APD$_{50}$ (ms) | APD$_{90}$ (ms) |
|---|---|---|---|---|
| Nodal-like | ~50 | <10 | <100 | <150 |
| Atrial-like | >50 | >10 | <100 | <150 |
| Ventricular-like | >50 | >10 | >100 | >150 |

Table 4 discloses AP parameters of spontaneously-firing and quiescent H7-derived cardiomyocytes. APs from n=20 cells were recorded and classified according to the criteria that are summarized in Table 3. All cells were classified as ventricular-like. Values are mean±s.e. APA: action potential amplitude; dV/dt: maximum upstroke velocity; APD90: action potential duration at 90% repolarization; APD50: action potential duration at 50% repolarization; MDP: maximum diastolic potential for spontaneous-firing cardiomyocytes; RMP: resting membrane potential for quiescent cardiomyocytes.

TABLE 4

| | Ventricular-like | |
|---|---|---|
| | Spontaneous-firing (n = 14) | Quiescent (n = 6) |
| APA (mV) | 91.97 ± 2.00 | 74.52 ± 10.57 |
| dV/dt (mV/ms) | 18.49 ± 3.57 | 11.63 ± 2.88 |
| Decay velocity (mV/ms) | −1.25 ± 0.10 | −0.95 ± 0.12 |
| APD50 (ms) | 142.75 ± 14.67 | 106.67 ± 7.31 |
| APD90 (ms) | 259.43 ± 30.05 | 134.17 ± 9.79 |
| MDP/RMP (mV) | −75.63 ± 1.45 | −55.70 ± 2.68 |

Taken together, these data demonstrate that small molecule-mediated directed differentiation of hESCs in accordance with the disclosure promotes the ventricular specification of hESC-derived cardiomyocytes.

Example 5

Functional Characterization of hESC-VCMs Derived Using the Efficient Protocol

The functionality as well as chamber-specific identity of the CMs derived using the efficient protocol were confirmed. Initially, electrophysiological profiles were obtained and analyzed from patch-clamp recordings and $Ca^{2+}$-imaging performed on 30- to 50-day-old single cells isolated from cardiogenic EBs. Of the 43 HES2-CMs recorded (from 5 independent batches), 93% displayed an action potential (AP) profile that was most consistent with the immature ventricular type CM[62, 66, 71] (FIGS. 5A & D). Immature traits such as spontaneous AP firing, a depolarized resting membrane potential or maximum diastolic potential, and Phase 4 depolarization were readily observed. AP parameters are summarized in Table 3. Consistent with AP data, when unselected cells isolated from HES2-EB were immunostained with MLC2v and cTnT, greater than 80% of the cells were both MLC2v- and cTnT-positive, indicating that the method (i.e., the efficient protocol) supports high-percentage VCM differentiation (FIG. 5B). After zeocin selection, 100% of LV-MLC2v-tdTomato-T2A-zeocin-transduced cells displayed typical ventricular-like APs. Therefore, the cells derived using the protocol were functional hESC-VCMs. As for $Ca^{2+}$ handling, FIG. 5C shows that transients from these cells had amplitudes and kinetics smaller and slower than those of adults[72, 73]. Furthermore, caffeine-induced $Ca^{2+}$ flux was also observed, indicating a functional sarcoplasmic reticulum (SR). Upon isoproterenol (Iso) application to the hESC-VCMs, a positive chronotropic response with increased spontaneous AP and $Ca^{2+}$ transient firings was observed. However, the transient amplitude remained unchanged (p>0.05) indicating a null ionotropic response to β-adrenergic stimulation. When switched to the voltage-clamp mode, signature ventricular ionic currents such as voltage-dependent $I_{Na}$, L-type $I_{Ca}$, $I_{Kr}$, sarcolemmal $I_{KATP}$ could be recorded (FIG. 6), electrophysiologically confirming the identity of the derived cells as VCMs.

Example 6

Immature Mitochondrial Structure of HES2-VCMs

Figure 7:
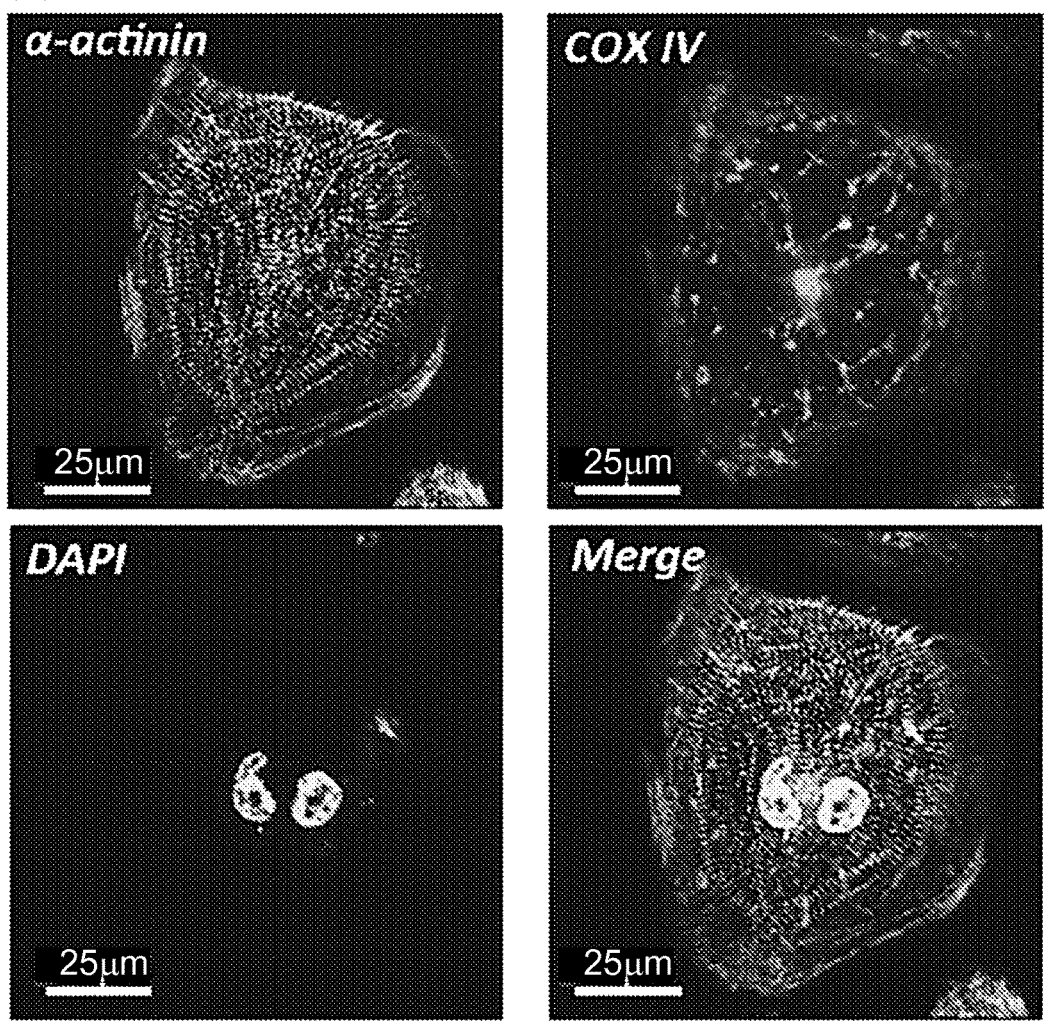
FIG. 7. Immature mitochondrial structure of HES2-VCMs. (A) LV-MLC2v-Tdtomato-T2A-Zeo transduced and Zeo-selected HES2-VCMs (30-50 day old) were Immunostained for α-actinin and mitochondrial cytochrome c oxidase (COX) IV. Nuclei were counterstained with DAPI (blue). Scale bar=25 μm. (B) HES2-VCMs were stained using the potential-sensitive JC-1 dye. Left panel shows representative image of control cells with both green and red fluorescence in the HES2-VCMs. Right panel shows representative image of HES2-VCMs subjected to 100 μM $H_2O_2$ (n=3). Scale bar=100 μm.
Figure 7:
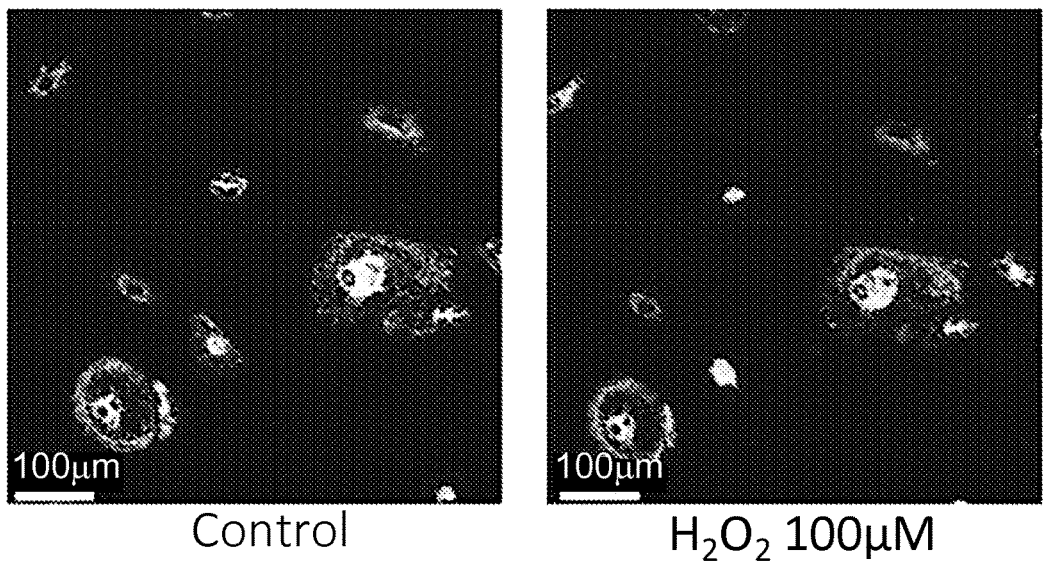

Others have reported that the structure of mitochondria reflects various stages of cardiogenesis[74, 75]. At day 30 post-differentiation, similar to embryonic/fetal CMs, HES2-VCMs displayed a perinuclear mitochondrial structure, as shown by staining with the mitochondrial COX IV specific antibody (FIG. 7A). In addition, the mitochondrial volume of HES2-VCMs was 33.7±0.4% (n=16) at day 30, smaller than the reported value of 40% in human adult CMs[76]. Therefore, HES2-VCMs were more comparable to fetal CMs, which also carry a lower mitochondrial mass with perinuclear localization compared to adult CMs[77]. The mitochondrial inner membrane potential of HES2-VCMs was examined next using the potential-sensitive JC-1 dye. FIG. 7B shows the appearance of both green and red fluorescence HES2-VCMs, demonstrating the presence of both depolarized (green monomer) and hyperpolarized (orange aggregate) mitochondrial membrane potential. Areas of depolarized mitochondrial membrane potential were found in the perinuclear region, while areas of hyperpolarized potential were mainly found at the perimeter of HES2-VCMs. Similar to primary CMs, when subjected to oxidative stress in the form of $H_2O_2$, hESC-VCMs showed a depolarization of their mitochondrial membrane potential (increase in green vs. orange fluorescence) with JC-1 orange/green intensity ratio decreased from 1.146 to 0.410.

Example 7

Figure 10:
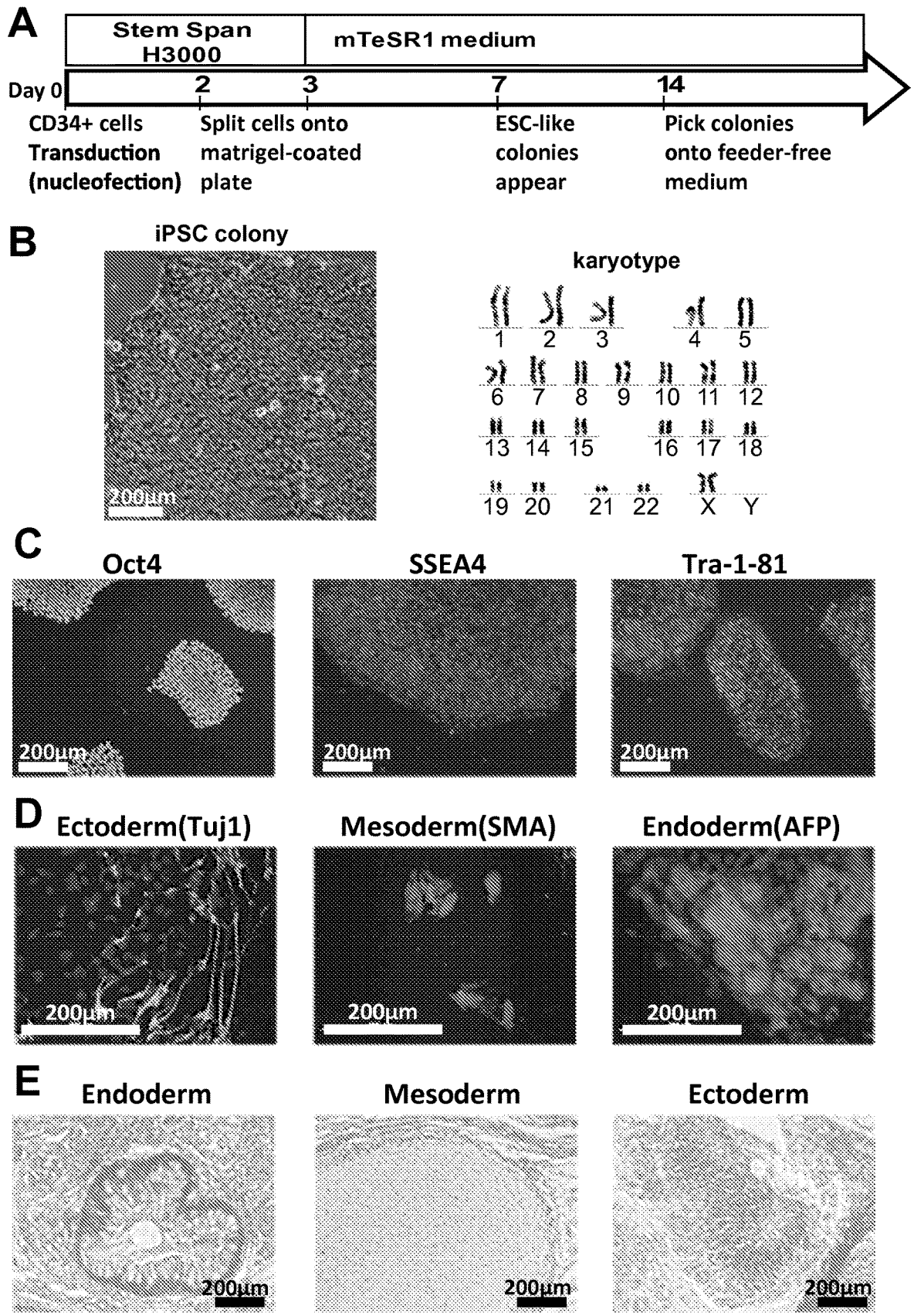
FIG. 10. Integration-free hiPSC generation and characterization. (A) Schematic diagram shows the generation of hiPSCs from human PB CD34+ or CB CD34+ cells using the episomal vectors as described in the Materials and Methods. (B) A representative karyograph of an iPSC clone. All analyzed PB and CB iPSC clones showed a normal karyotype. (C) PB2 and CB80 iPSCs express pluripotency markers Oct-4, SSEA4 and Tra-1-81 by immunostaining. Representative images are shown with scale bar=200 μm. (D) A representative images show hiPSCs form three germ layers from spontaneous differentiation in vitro. (e) PB2 and CD80 iPSCs form teratoma in immunodeficient mice. H & E staining of representative teratoma from PB2 iPSCs shows derivatives of 3 embryonic germ layers. Scale bar=200 μm.

Ventricular Specification of hiPSCs Reprogrammed from Human CD34+ Cells and Additional hESC Lines Given that most methods for directed cardiac differentiation require line-dependent optimizations of growth factors[46, 48, 49, 60], the versatility of the efficient protocol was examined to assess the consistency of hPSC-VCM yields with different cell lines. Distinct hESC lines having different cardiogenic potentials has been reported[78]. These differences can be further exemplified in hiPSCs, which are known to display significant line-to-line and clone-to-clone variability. Therefore, we generated hiPSCs from neonatal CB or adult PB CD34+ cells using non-viral episomal vectors. Two representative hiPSC lines generated from CB CD34+ (iPSC-CB80) and PB CD34+ cells (iPSC-PB2) retained a normal karyotype, stained positively for pluripotency markers by immunocytochemistry, and expressed high levels of Oct4 and Rex1. Differentiation into three germ layers was confirmed by qRT-PCR and immunostaining. When injected subcutaneously into immunodeficient mice, all tested hiPSC lines formed teratomas consisting of the three primitive germ layers (FIG. 10). When these hiPSC lines were subjected to ventricular specification by a protocol disclosed herein, spontaneously contracting cardiogenic EBs routinely emerged on day 8-9 and achieved about 80% cTnT+ cells (FIG. 3), which also expressed the cardiac

TABLE 5

Action potential properties of HES2-VCMs (n = 28).

| Firing Frequency (Hz) | Amplitude (mV) | Upstroke velocity (mV/ms) | Decay velocity (mV/ms) | APD50 (ms) | APD90 (ms) | MDP (mV) |
|---|---|---|---|---|---|---|
| 1.59 ± 0.03 | 94.0 ± 0.4 | 8.85 ± 0.31 | −0.76 ± 0.01 | 443.0 ± 8.4 | 571.4 ± 9.0 | −72.5 ± 0.2 | markers cTnT, α-actinin, MLC2a, and exhibited immature signature ventricular AP and Ca$^{2+}$ transients (FIG. 5). When tested with additional hESC lines H7 and H9, qualitatively similar data in terms of time when beating EBs first appeared, % of cTnT$^+$ cells, AP and Ca$^{2+}$ transients were also consistently observed (FIGS. 3 and 5).

Example 8

Transplantation of hPSC-VCM for In Vivo Studies

Figure 8:
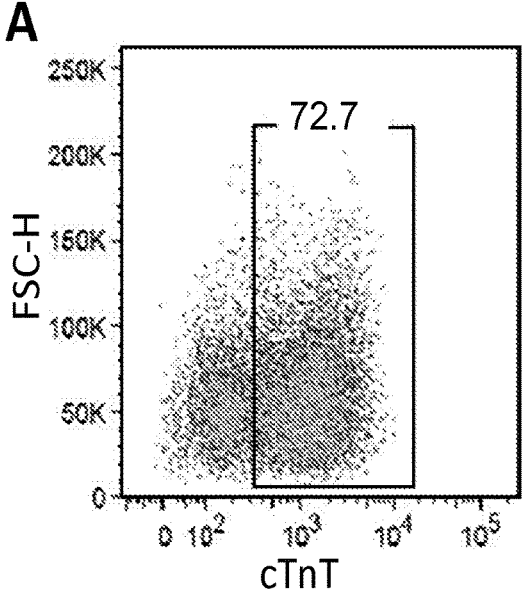
FIG. 8. In vivo survival of H9-VCM under kidney capsule transplantation. (A) $H9^{DF}$ was used to differentiate VCM. Differentiation efficiency was estimated based on cTnT protein expression by flow cytometry. Representative FACS plot is shown. (B) In vivo bioluminescence imaging (BLI) signal measured from animals in which $H9^{DF}$-VCMs were transplanted into the kidney capsule. (C) A representative animal imaged following transplantation of $2\times10^5$ $H9^{DF}$-VCMs into the kidney capsule. Color scale bar value represents photons/sec/$cm^2$/steridian (p/s/$cm^2$/sr). (D) Immunohistochemistry for cTNT-positive cells in the transplanted kidneys harvested on d28. Scale bar=100 μm.
Figure 8:
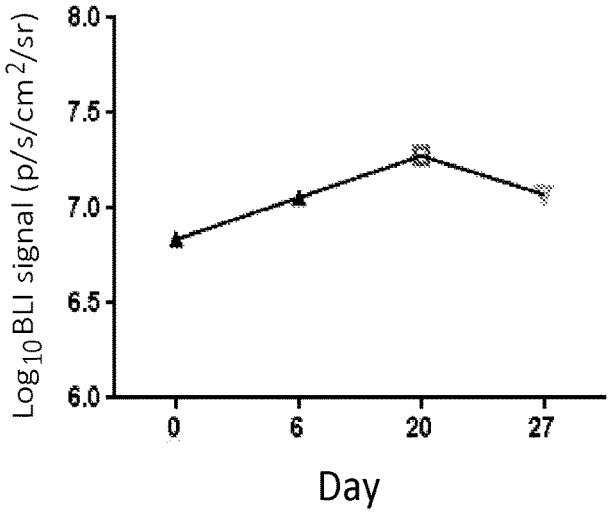
Figure 8:
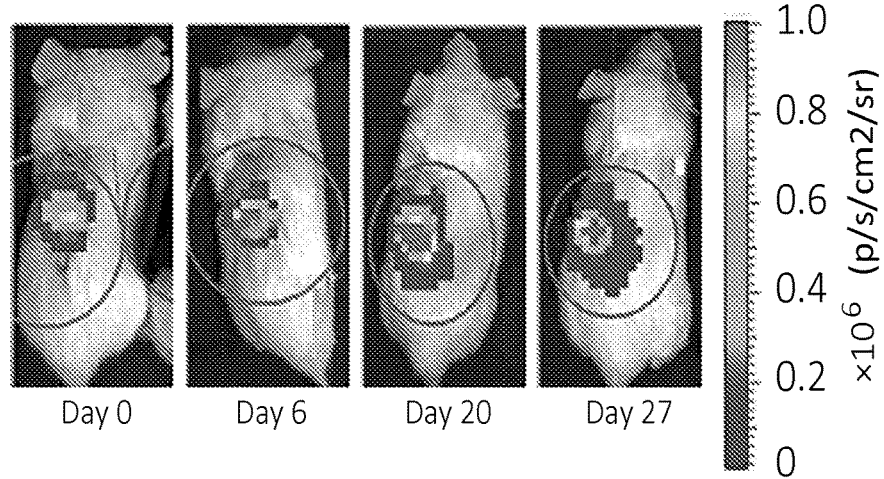
Figure 8:
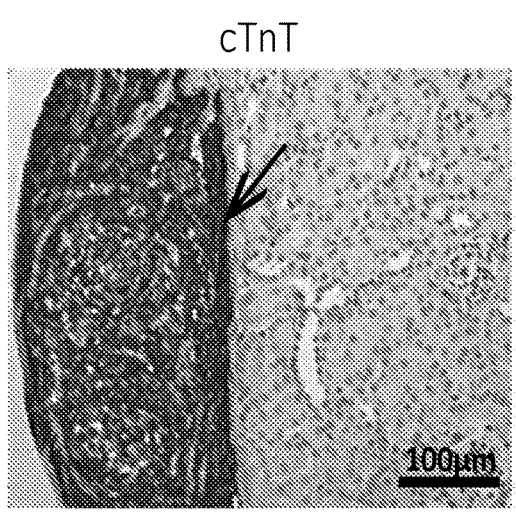
Figure 8:
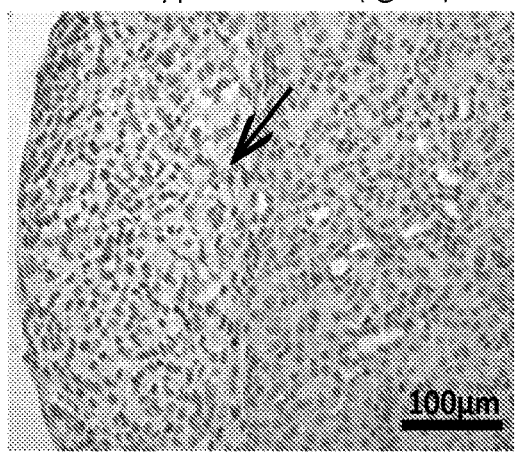

Transplantation studies of hESC-CMs have almost always involved cell mixtures with low yields of hESC-CMs or heterogeneous mixtures of V and other chamber-specific types[69, 79]. To test the in vivo survival of the hPSC-VCMs disclosed herein, the protocol was followed to differentiate a H9$^{DF}$ cell line expressing the double fusion GFP-luciferase proteins to H9$^{DF}$-VCMs[69]. FIG. 8A shows that greater than 70% cTnT$^+$ cells could be generated. After transplantation into the kidney capsule of immunodeficient mice, cTnT+ cells remained detected for least 27 days (FIGS. 8B & C). Immunohistochemistry staining showed a localized region of cTnT-positive cells in the transplanted kidney capsule (FIG. 8D). Therefore, the robust differentiation of VCM of hPSC provides a great cell source for disease treatment, such as transplantations.

Each of the references cited below is incorporated by reference herein in its entirety, or in relevant part, as would be apparent from context. The references are cited throughout this disclosure using superscripted numbers corresponding to the following numbered reference list.

REFERENCES

1. Evans, S. M., Yelon, D., Conlon, F. L. & Kirby, M. L. Myocardial lineage development. Circ Res 107, 1428-1444 (2010).
2. Olson, E. N. Gene regulatory networks in the evolution and development of the heart. Science 313, 1922-1927 (2006).
3. Noseda, M., Peterkin, T., Simoes, F. C., Patient, R. & Schneider, M. D. Cardiopoietic factors: extracellular signals for cardiac lineage commitment. Circ Res 108, 129-152 (2011).
4. Kehat, I. et al. Human embryonic stem cells can differentiate into myocytes with structural and functional properties of cardiomyocytes. J Clin Invest 108, 407-414 (2001).
5. Laflamme, M. A. et al. Cardiomyocytes derived from human embryonic stem cells in pro-survival factors enhance function of infarcted rat hearts. Nat Biotechnol 25, 1015-1024 (2007).
6. Yang, L. et al. Human cardiovascular progenitor cells develop from a KDR+ embryonic-stem-cell-derived population. Nature 453, 524-528 (2008).
7. He, J. Q., Ma, Y., Lee, Y., Thomson, J. A. & Kamp, T. J. Human embryonic stem cells develop into multiple types of cardiac myocytes: action potential characterization. Circ Res 93, 32-39 (2003).
8. Mummery, C. et al. Differentiation of human embryonic stem cells to cardiomyocytes: role of coculture with visceral endoderm-like cells. Circulation 107, 2733-2740 (2003).
9. Xu, C., Police, S., Rao, N. & Carpenter, M. K. Characterization and enrichment of cardiomyocytes derived from human embryonic stem cells. Circ Res 91, 501-508 (2002).
10. Anderson, D. et al. Transgenic enrichment of cardiomyocytes from human embryonic stem cells. Mol Ther 15, 2027-2036 (2007).
11. Kita-Matsuo, H. et al. Lentiviral vectors and protocols for creation of stable hESC lines for fluorescent tracking and drug resistance selection of cardiomyocytes. PLoS One 4, e5046 (2009).
12. Huber, I. et al. Identification and selection of cardiomyocytes during human embryonic stem cell differentiation. FASEB J 21, 2551-2563 (2007).
13. Ao, A., Hao, J. & Hong, C. C. Regenerative chemical biology: current challenges and future potential. Chem Biol 18, 413-424 (2011).
14. Wu, X., Ding, S., Ding, Q., Gray, N. S. & Schultz, P. G. Small molecules that induce cardiomyogenesis in embryonic stem cells. J Am Chem Soc 126, 1590-1591 (2004).
15. Takahashi, T. et al. Ascorbic acid enhances differentiation of embryonic stem cells into cardiac myocytes. Circulation 107, 1912-1916 (2003).
16. Sadek, H. et al. Cardiogenic small molecules that enhance myocardial repair by stem cells. Proc Natl Acad Sci USA 105, 6063-6068 (2008).
17. Diamandis, P. et al. Chemical genetics reveals a complex functional ground state of neural stem cells. Nat Chem Biol 3, 268-273 (2007).
18. Borowiak, M. et al. Small molecules efficiently direct endodermal differentiation of mouse and human embryonic stem cells. Cell Stem Cell 4, 348-358 (2009).
19. Chen, G., Hou, Z., Gulbranson, D. R. & Thomson, J. A. Actin-myosin contractility is responsible for the reduced viability of dissociated human embryonic stem cells. Cell Stem Cell 7, 240-248 (2010).
20. Ohgushi, M. et al. Molecular pathway and cell state responsible for dissociation-induced apoptosis in human pluripotent stem cells. Cell Stem Cell 7, 225-239 (2010).
21. Keller, G. M. In vitro differentiation of embryonic stem cells. Curr Opin Cell Biol 7, 862-869 (1995).
22. Jaenisch, R. & Young, R. Stem cells, the molecular circuitry of pluripotency and nuclear reprogramming. Cell 132, 567-582 (2008).
23. Kispert, A., Herrmann, B. G., Leptin, M. & Reuter, R. Homologs of the mouse Brachyury gene are involved in the specification of posterior terminal structures in *Drosophila*, *Tribolium*, and *Locusta*. Genes Dev 8, 2137-2150 (1994).
24. Ng, E. S. et al. The primitive streak gene Mixl1 is required for efficient haematopoiesis and BMP4-induced ventral mesoderm patterning in differentiating ES cells. Development 132, 873-884 (2005).
25. Saga, Y., Kitajima, S. & Miyagawa-Tomita, S. Mesp1 expression is the earliest sign of cardiovascular development. Trends Cardiovasc Med 10, 345-352 (2000).
26. Bondue, A. et al. Mesp1 acts as a master regulator of multipotent cardiovascular progenitor specification. Cell Stem Cell 3, 69-84 (2008).
27. Buckingham, M., Meilhac, S. & Zaffran, S. Building the mammalian heart from two sources of myocardial cells. Nat Rev Genet 6, 826-835 (2005).
28. Moretti, A. et al. Multipotent embryonic isl1+ progenitor cells lead to cardiac, smooth muscle, and endothelial cell diversification. Cell 127, 1151-1165 (2006).
29. Chen, B. et al. Small molecule-mediated disruption of Wnt-dependent signaling in tissue regeneration and cancer. Nat Chem Biol 5, 100-107 (2009).
30. Chuva de Sousa Lopes, S. M. et al. Patterning the heart, a template for human cardiomyocyte development. Dev Dyn 235, 1994-2002 (2006).

31. Glukhova, M. A., Frid, M. G. & Koteliansky, V. E. Developmental changes in expression of contractile and cytoskeletal proteins in human aortic smooth muscle. J Biol hem 265, 13042-13046 (1990).
32. Bers, D. M. Cardiac excitation-contraction coupling. Nature 415, 198-205 (2002).
33. Weinberg, S., Lipke, E. A. & Tung, L. In vitro electrophysiological mapping of stem cells. Methods Mol Biol 660, 215-237 (2010).
34. Glukhov, A. V. et al. Transmural dispersion of repolarization in failing and nonfailing human ventricle. Circ Res 106, 981-991 (2010).
35. Feldman, D. S., Carnes, C. A., Abraham, W. T. & Bristow, M. R. Mechanisms of disease: beta-adrenergic receptors—alterations in signal transduction and pharmacogenomics in heart failure. Nat Clin Pract Cardiovasc Med 2, 475-483 (2005).
36. Ueno, S. et al. Biphasic role for Wnt/beta-catenin signaling in cardiac specification in zebrafish and embryonic stem cells. Proc Natl Acad Sci USA 104, 9685-9690 (2007).
37. Naito, A. T. et al. Developmental stage-specific biphasic roles of Wnt/beta-catenin signaling in cardiomyogenesis and hematopoiesis. Proc Natl Acad Sci USA 103, 19812-19817 (2006).
38. Gessert, S. & Kuhl, M. The multiple phases and faces of wnt signaling during cardiac differentiation and development. Circ Res 107, 186-199 (2010).
39. Ludwig, T. E. et al. Feeder-independent culture of human embryonic stem cells. Nat Methods 3, 637-646 (2006).
40. Moore, J. C. et al. Distinct cardiogenic preferences of two human embryonic stem cell (hESC) lines are imprinted in their proteomes in the pluripotent state. Biochem Biophys Res Commun 372, 553-558 (2008).
41. Galende E, Karakikes I, Edelmann L, Desnick R J, Kerenyi T, Khoueiry G, Lafferty J, McGinn J T, Brodman M, Fuster V, Hajjar R J, Polgar K. Amniotic fluid cells are more efficiently reprogrammed to pluripotency than adult cells. Cell Reprogram. 2010; 12:117-125.
42. Ludwig T E, Bergendahl V, Levenstein M E, Yu J, Probasco M D, Thomson J A. Feeder-independent culture of human embryonic stem cells. Nat Methods. 2006; 3:637-646.
43. Huber I, Itzhaki I, Caspi O, Arbel G, Tzukerman M, Gepstein A, Habib M, Yankelson L, Kehat I, Gepstein L. Identification and selection of cardiomyocytes during human embryonic stem cell differentiation. FASEB J. 2007; 21:2551-2563.
44. Moore J C, Fu J, Chan Y C, Lin D, Tran H, Tse H F, Li R A. Distinct cardiogenic preferences of two human embryonic stem cell (hesc) lines are imprinted in their proteomes in the pluripotent state. Biochem Biophys Res Commun. 2008; 372:553-558.
45. Weinberg S, Lipke E A, Tung L. In vitro electrophysiological mapping of stem cells. Methods Mol Biol. 2010; 660:215-237.
46. Kattman S J, A D Witty, M Gagliardi, N C Dubois, M Niapour, A Hotta, J Ellis and G Keller. (2011). Stage-specific optimization of activin/nodal and BMP signaling promotes cardiac differentiation of mouse and human pluripotent stem cell lines. Cell Stem Cell 8:228-40.
47. Zhang J, M Klos, G F Wilson, A M Herman, X Lian, K K Raval, M R Barron, L Hou, A G Soerens, J Yu, S P Palecek, G E Lyons, J A Thomson, T J Herron, J Jalife and T J Kamp. (2012). Extracellular matrix promotes highly efficient cardiac differentiation of human pluripotent stem cells: the matrix sandwich method. Circ Res 111:1125-36.
48. Yang L, M H Soonpaa, E D Adler, T K Roepke, S J Kattman, M Kennedy, E Henckaerts, K Bonham, G W Abbott, R M Linden, U Field and G M Keller. (2008). Human cardiovascular progenitor cells develop from a KDR+ embryonic-stem-cell-derived population. Nature 453:524-8.
49. Burridge P W, S Thompson, M A Millrod, S Weinberg, X Yuan, A Peters, V Mahairaki, V E Koliatsos, L Tung and E T Zambidis. (2011). A universal system for highly efficient cardiac differentiation of human induced pluripotent stem cells that eliminates interline variability. PLoS One 6:e18293.
50. Burridge P W and E T Zambidis. (2013). Highly efficient directed differentiation of human induced pluripotent stem cells into cardiomyocytes. Methods Mol Biol 997: 149-61.
51. Lecina M, S Ting, A Choo, S Reuveny and S Oh. (2010). Scalable platform for human embryonic stem cell differentiation to cardiomyocytes in suspended microcarrier cultures. Tissue Eng Part C Methods 16:1609-19.
52. Lian X, J Zhang, S M Azarin, K Zhu, L B Hazeltine, X Bao, C Hsiao, T J Kamp and S P Palecek. (2013). Directed cardiomyocyte differentiation from human pluripotent stem cells by modulating Wnt/beta-catenin signaling under fully defined conditions. Nat Protoc 8:162-75.
53. Kehat I, D Kenyagin-Karsenti, M Snir, H Segev, M Amit, A Gepstein, E Livne, O Binah, J Itskovitz-Eldor and L Gepstein. (2001). Human embryonic stem cells can differentiate into myocytes with structural and functional properties of cardiomyocytes. J Clin Invest 108:407-14.
54. He J Q, Y Ma, Y Lee, J A Thomson and T J Kamp. (2003). Human embryonic stem cells develop into multiple types of cardiac myocytes: action potential characterization. Circ Res 93:32-9.
55. Mummery C, D Ward-van Oostwaard, P Doevendans, R Spijker, S van den Brink, R Hassink, M van der Heyden, T Opthof, M Pera, A B de la Riviere, R Passier and L Tertoolen. (2003). Differentiation of human embryonic stem cells to cardiomyocytes: role of coculture with visceral endoderm-like cells. Circulation 107:2733-40.
56. Passier R and C Mummery. (2003). Origin and use of embryonic and adult stem cells in differentiation and tissue repair. Cardiovasc Res 58:324-35.
57. Lian X, C Hsiao, G Wilson, K Zhu, L B Hazeltine, S M Azarin, K K Raval, J Zhang, T J Kamp and S P Palecek. (2012). Robust cardiomyocyte differentiation from human pluripotent stem cells via temporal modulation of canonical Wnt signaling. Proc Natl Acad Sci USA 109: E1848-57.
58. Minami I, K Yamada, T G Otsuji, T Yamamoto, Y Shen, S Otsuka, S Kadota, N Morone, M Barve, Y Asai, T Tenkova-Heuser, J E Heuser, M Uesugi, K Aiba and N Nakatsuji. (2012). A small molecule that promotes cardiac differentiation of human pluripotent stem cells under defined, cytokine- and xeno-free conditions. Cell Rep 2:1448-60.
59. Ren Y, M Y Lee, S Schliffke, J Paavola, P J Amos, X Ge, M Ye, S Zhu, G Senyei, L Lum, B E Ehrlich and Y Qyang. (2011). Small molecule Wnt inhibitors enhance the efficiency of BMP-4-directed cardiac differentiation of human pluripotent stem cells. J Mol Cell Cardiol 51:280-7.
60. Elliott D A, S R Braam, K Koutsis, E S Ng, R Jenny, E L Lagerqvist, C Biben, T Hatzistavrou, C E Hirst, Q C Yu, R J Skelton, D Ward-van Oostwaard, S M Lim, O Khammy, X Li, S M Hawes, R P Davis, A L Goulburn, R Passier, O W Prall, J M Haynes, C W Pouton, D M Kaye, C L Mummery, A G Elefanty and E G Stanley. (2011). NKX2-5(eGFP/w) hESCs for isolation of human cardiac progenitors and cardiomyocytes. Nat Methods 8:1037-40.
61. Zhang J, G F Wilson, A G Soerens, C H Koonce, J Yu, S P Palecek, J A Thomson and T J Kamp. (2009).

Functional cardiomyocytes derived from human induced pluripotent stem cells. Circ Res 104:e30-41.
62. Moore J C, J Fu, Y C Chan, D Lin, H Tran, H F Tse and R A Li. (2008). Distinct cardiogenic preferences of two human embryonic stem cell (hESC) lines are imprinted in their proteomes in the pluripotent state. Biochem Biophys Res Commun 372:553-8.
63. Okita K, Y Matsumura, Y Sato, A Okada, A Morizane, S Okamoto, H Hong, M Nakagawa, K Tanabe, K Tezuka, T Shibata, T Kunisada, M Takahashi, J Takahashi, H Saji and S Yamanaka. (2011). A more efficient method to generate integration-free human iPS cells. Nat Methods 8:409-12.
64. Bates S E. (2011). Classical cytogenetics: karyotyping techniques. Methods Mol Biol 767:177-90.
65. Fu J D, P Jiang, S Rushing, J Liu, N Chiamvimonvat and R A Li. (2010). Na+/Ca2+ exchanger is a determinant of excitation-contraction coupling in human embryonic stem cell-derived ventricular cardiomyocytes. Stem Cells Dev 19:773-82.
66. Chow M Z, L Geng, C W Kong, W Keung, J C Fung, K Boheler and R A Li. (2013). Epigenetic regulation of the electrophysiological phenotype of human embryonic stem cell-derived ventricular cardiomyocytes: Insights for driven maturation and hypertrophic growth. Stem Cells Dev.
67. Fu J D, S N Rushing, D K Lieu, C W Chan, C W Kong, L Geng, K D Wilson, N Chiamvimonvat, K R Boheler, J C Wu, G Keller, R J Hajjar and R A Li. (2011). Distinct roles of microRNA-1 and -499 in ventricular specification and functional maturation of human embryonic stem cell-derived cardiomyocytes. PLoS One 6:e27417.
68. Swijnenburg R J, S Schrepfer, J A Govaert, F Cao, K Ransohoff, A Y Sheikh, M Haddad, A J Connolly, M M Davis, R C Robbins and J C Wu. (2008). Immunosuppressive therapy mitigates immunological rejection of human embryonic stem cell xenografts. Proc Natl Acad Sci USA 105:12991-6.
69. Cao F, R A Wagner, K D Wilson, X Xie, J D Fu, M Drukker, A Lee, R A Li, S S Gambhir, I L Weissman, R C Robbins and J C Wu. (2008). Transcriptional and functional profiling of human embryonic stem cell-derived cardiomyocytes. PLoS One 3:e3474.
70. Passier R, D W Oostwaard, J Snapper, J Kloots, R J Hassink, E Kuijk, B Roelen, A B de la Riviere and C Mummery. (2005). Increased cardiomyocyte differentiation from human embryonic stem cells in serum-free cultures. Stem Cells 23:772-80.
71. Lieu D K, J D Fu, N Chiamvimonvat, K C Tung, G P McNerney, T Huser, G Keller, C W Kong and R A Li. (2013). Mechanism-based facilitated maturation of human pluripotent stem cell-derived cardiomyocytes. Circ Arrhythm Electrophysiol 6:191-201.
72. Liu J, J D Fu, C W Siu and R A Li. (2007). Functional sarcoplasmic reticulum for calcium handling of human embryonic stem cell-derived cardiomyocytes: insights for driven maturation. Stem Cells 25:3038-44.
73. Liu J, D K Lieu, C W Siu, J D Fu, H F Tse and R A Li. (2009). Facilitated maturation of Ca2+ handling properties of human embryonic stem cell-derived cardiomyocytes by calsequestrin expression. Am J Physiol Cell Physiol 297:C152-9.
74. Folmes C D, P P Dzeja, T J Nelson and A Terzic. (2012). Mitochondria in control of cell fate. Circ Res 110:526-9.
75. Horn J R, R A Quintanilla, D L Hoffman, K L de Mesy Bentley, J D Molkentin, S S Sheu and G A Porter, Jr. (2011). The permeability transition pore controls cardiac mitochondrial maturation and myocyte differentiation. Dev Cell 21:469-78.
76. Huang X, L Sun, S Ji, T Zhao, W Zhang, J Xu, J Zhang, Y Wang, X Wang, C Franzini-Armstrong, M Zheng and H Cheng. (2013). Kissing and nanotunneling mediate intermitochondrial communication in the heart. Proc Natl Acad Sci USA 110:2846-51.
77. Pohjoismaki J L, M Kruger, N Al-Furoukh, A Lagerstedt, P J Karhunen and T Braun. (2013). Postnatal cardiomyocyte growth and mitochondrial reorganization cause multiple changes in the proteome of human cardiomyocytes. Mol Biosyst 9:1210-9.
78. Moore J C, S Y Tsang, S N Rushing, D Lin, H F Tse, C W Chan and R A Li. (2008). Functional consequences of overexpressing the gap junction Cx43 in the cardiogenic potential of pluripotent human embryonic stem cells. Biochem Biophys Res Commun 377:46-51.
79. Pearl J I, A S Lee, D B Leveson-Gower, N Sun, Z Ghosh, F Lan, J Ransohoff, R S Negrin, M M Davis and J C Wu. (2011). Short-term immunosuppression promotes engraftment of embryonic and induced pluripotent stem cells. Cell Stem Cell 8:309-17.
80. Kim et al., (2013) Nature 494:105-110.

The disclosed subject matter has been described with reference to various specific and preferred embodiments and techniques. It should be understood, however, that many variations and modifications may be made while remaining within the spirit and scope of the disclosed subject matter.

What is claimed is:

1. A method of generating a cardiogenic embryoid body comprising at least one ventricular-like cardiomyocyte, said method comprising incubating a non-terminally differentiated human cell in suspension under serum-free, feeder-free culture conditions, wherein said incubating comprises the following sequential steps:

(a) culturing the non-terminally differentiated human cell for 24 to 72 hours in a suspension consisting essentially of basement membrane preparation extracted from Engelbreth-Holm-Swarm mouse sarcoma, a culture medium for cells that have not terminally differentiated, bone morphogenetic protein 4 (BMP4), and Rho kinase inhibitor;

(b) incubating the culture for 3 to 5 days in a suspension consisting essentially of the basement membrane preparation, a serum-free medium formulated to support the growth of human hematopoietic progenitor cells, ascorbic acid, L-alanyl-L-glutamine, BMP4, and activin-A; and (c) growing the culture for at least four days in a suspension consisting essentially of the basement membrane preparation, the serum-free medium, ascorbic acid, L-alanyl-L-glutamine, BMP4, activin-A, and Inhibitor of Wnt Response 1 (IWR-1) to generate a culture of cardiomyocytes with a yield of at least 90% ventricular-like cardiomyocytes.

2. The method according to claim 1, wherein the non-terminally differentiated human cell is a human embryonic stem cell, a human adult stem cell, or a human induced pluripotent stem cell.

3. The method according to claim 1, wherein at least 93% of the cultured cardiomyocytes are cardiac Troponin T+ (cTNT+).

4. The method according to claim 1, wherein the ventricular-like cardiomyocytes exhibit a detectable chronotropic response to β-adrenergic stimulation.

5. The method according to claim 1, wherein at least 70 the ventricular-like cardiomyocytes are obtained from each non-terminally differentiated human cell.

6. The method according to claim 5 wherein the non-terminally differentiated human cell is a human pluripotent stem cell (hPSC).

7. The method according to claim 1, wherein the non-terminally differentiated human cell is obtained from a subject in need of progenitor cell therapy.

8. The method according to claim 1 further comprising the following steps:
  (d) maintaining the cardiomyocyte culture in the serum-free medium and ascorbic acid; and
  (e) incubating the cardiomyocytes in media comprising a neurohumoral agent and a histone deacetylase inhibitor, exposing the cardiomyocytes to at least one stressor, and contacting the cardiomyocytes with an adrenergic/cholinergic agonist.

9. A method of generating a cardiogenic embryoid body comprising ventricular-like cardiomyocytes, the method comprising incubating a non-terminally differentiated human cell in suspension under serum-free, feeder-free culture conditions, wherein the non-terminally differentiated human cell is a human embryonic stem cell, a human adult stem cell, or a human induced pluripotent stem cell, wherein the incubating comprises the following sequential steps:
  (a) culturing the non-terminally differentiated human cell for 24 hours in a suspension consisting essentially of basement membrane preparation extracted from Engelbreth-Holm-Swarm mouse sarcoma, a culture medium for cells that have not terminally differentiated, 0.5-20 ng/ml bone morphogenetic protein 4 (BMP4), and 5-50 µM Rho kinase inhibitor;
  (b) incubating the culture for 3 days in a suspension consisting essentially of the basement membrane preparation, a serum-free medium formulated to support the growth of human hematopoietic progenitor cells, 50 µg/ml ascorbic acid, 2 mM L-alanyl-L-glutamine, 0.5-20 ng/ml BMP4, and 2-25 ng/ml activin-A; and
  (c) growing the culture for at least four days in a suspension consisting essentially of the basement membrane preparation, the serum-free medium, 50 µg/ml ascorbic acid, 2 mM L-alanyl-L-glutamine, 0.5-20 ng/ml BMP4, 2-25 ng/ml activin-A, and 4-7 µM Inhibitor of Wnt Response 1 (IWR-1) to generate a culture of cardiomyocytes with a yield of at least 90% ventricular-like cardiomyocytes.

10. The method according to claim 9 further comprising the following steps:
  (d) maintaining the cardiomyocyte culture in the serum-free medium and 50 µg/ml ascorbic acid; and
  (e) incubating the cardiomyocytes in media comprising a neurohumoral agent selected from the group consisting of thyroid hormone T3 and an adrenergic agonist, and a histone deacetylase inhibitor, wherein the histone deacetylase inhibitor is valproic acid; exposing the cardiomyocytes to at least one stressor; and contacting the cardiomyocytes with an adrenergic/cholinergic agonist to generate mature cardiomyocytes, wherein the adrenergic agonist is selected from the group consisting of epinephrine, nor-epinephrine, adrenaline, an alpha-1A adrenergic agonist, an alpha-1B adrenergic agonist, an alpha-1D adrenergic agonist, an alpha-2A adrenergic agonist, an alpha-2B adrenergic agonist, an alpha-2C adrenergic agonist, a beta-1 adrenergic agonist, a beta-2 adrenergic agonist, and a beta-3 adrenergic agonist.

11. The method according to claim 9, wherein in step (a) the amount of BMP-4 is 1 ng/ml and the amount of Rho kinase inhibitor is 10 µM, wherein in steps (b) and (c) the amount of BMP4 is 10 ng/ml and the amount of activin-A is 10 ng/ml, and wherein in step (c) the amount of IWR-1 is 5 µM.

12. The method according to claim 9, wherein at least 93% of the cultured cardiomyocytes are cardiac Troponin T+ (cTNT+).

13. The method according to claim 9, wherein the ventricular-like cardiomyocytes exhibit a detectable chronotropic response to β-adrenergic stimulation.

* * * * *